(12) United States Patent
Tapocik

(10) Patent No.: US 8,985,394 B1
(45) Date of Patent: Mar. 24, 2015

(54) PEN REMOVABLY RETAINING SINGLE USE CAPSULE CONTAINING TOOTH WHITENING COMPOUNDS, DENTAL BONDING COMPOUNDS AND ADHESIVES AND REMOVABLY RETAINING DISPOSABLE TOOTH WHITENING APPLICATORS, DISPOSABLE DENTAL BONDING COMPOUND APPLICATORS AND DISPOSABLE ADHESIVE APPLICATORS

(71) Applicant: Bryan Tapocik, Highland, CA (US)

(72) Inventor: Bryan Tapocik, Highland, CA (US)

( * ) Notice: Subject to any disclaimer, the term of this patent is extended or adjusted under 35 U.S.C. 154(b) by 0 days.

(21) Appl. No.: 14/087,401

(22) Filed: Nov. 22, 2013

(51) Int. Cl.
| | | |
|---|---|---|
| *B67D 1/00* | (2006.01) | |
| *A61C 19/00* | (2006.01) | |
| *A47K 5/12* | (2006.01) | |

(52) U.S. Cl.
CPC .............. *A61C 19/005* (2013.01); *A47K 5/1204* (2013.01)
USPC .............................................. 222/82; 222/325

(58) Field of Classification Search
CPC ............................. A61C 19/005; A47K 5/1204
USPC ............ 222/82, 391, 386.137, 325–327, 362, 222/386, 145.5, 160, 165
See application file for complete search history.

(56) References Cited

U.S. PATENT DOCUMENTS

| | | | |
|---|---|---|---|
| 4,121,739 A | 10/1978 | Devaney | |
| 5,092,842 A * | 3/1992 | Bechtold et al. | 604/135 |
| 5,104,005 A | 4/1992 | Schneider, Jr. | |
| 5,310,091 A | 5/1994 | Dunning et al. | |
| 5,333,760 A | 8/1994 | Simmen | |
| 5,535,922 A | 7/1996 | Maziarz | |
| 5,611,687 A | 3/1997 | Wagner | |
| 5,743,436 A * | 4/1998 | Wilcox et al. | 222/137 |
| 6,048,201 A * | 4/2000 | Zwingenberger | 433/90 |
| 6,116,900 A | 9/2000 | Ostler | |
| 6,176,632 B1 | 1/2001 | Kageyama et al. | |
| 6,227,739 B1 | 5/2001 | Kageyama | |
| 6,283,660 B1 | 9/2001 | Furlong et al. | |
| 6,918,515 B2 | 7/2005 | Noguchi | |
| 7,201,527 B2 | 4/2007 | Thorpe et al. | |
| 7,344,375 B2 * | 3/2008 | Mukasa et al. | 433/90 |
| 7,748,980 B2 | 7/2010 | Mulhauser et al. | |
| 7,794,166 B2 | 9/2010 | Zhang | |
| 7,882,983 B2 | 2/2011 | Reidt et al. | |
| 7,976,489 B2 * | 7/2011 | Lawter et al. | 604/63 |
| 7,980,778 B2 | 7/2011 | Akaishi et al. | |
| 8,096,449 B2 | 1/2012 | Keller | |
| 8,328,449 B2 | 12/2012 | Wightman et al. | |
| 2005/0063766 A1 | 3/2005 | Chen et al. | |
| 2006/0275225 A1 | 12/2006 | Prencipe et al. | |
| 2007/0086830 A1 | 4/2007 | Kageyama | |

(Continued)

FOREIGN PATENT DOCUMENTS

| | | | |
|---|---|---|---|
| JP | 096151123 A | 6/1997 | |
| JP | 2007130437 A | 5/2007 | |

*Primary Examiner* — Lien Ngo
(74) *Attorney, Agent, or Firm* — Thomas I. Rozsa

(57) ABSTRACT

The present invention involves the field of numerous types of compounds including tooth whitening compounds and in particular, to specific apparatus which are used to retain tooth whitening compounds and then dispense them either into a dental tray where the tray is placed over the patient's teeth for a period of time or the tooth whitening compound is directly applied to the patient's teeth by the dentist or the dental assistant. More broadly described, the present invention includes compound and applicators used to dispense the compounds including tooth whitening compounds, dental bonding and filling compounds, adhesives, finely ground powder, jells, creams and paints.

22 Claims, 20 Drawing Sheets

(56) References Cited

U.S. PATENT DOCUMENTS

| | | |
|---|---|---|
| 2008/0274066 A1 | 11/2008 | Montgomery |
| 2009/0095777 A1 | 4/2009 | Francavilla |
| 2009/0247915 A1* | 10/2009 | Imboden et al. ............... 601/70 |
| 2010/0114025 A1* | 5/2010 | Moller .......................... 604/135 |
| 2010/0298781 A1* | 11/2010 | Hogdahl et al. .............. 604/214 |
| 2011/0129288 A1 | 6/2011 | Uehara |

\* cited by examiner

PEN REMOVABLY RETAINING SINGLE USE CAPSULE CONTAINING TOOTH WHITENING COMPOUNDS, DENTAL BONDING COMPOUNDS AND ADHESIVES AND REMOVABLY RETAINING DISPOSABLE TOOTH WHITENING APPLICATORS, DISPOSABLE DENTAL BONDING COMPOUND APPLICATORS AND DISPOSABLE ADHESIVE APPLICATORS

BACKGROUND OF THE INVENTION

1. Field of the Invention

The present invention relates to the field of compounds which include but are not limited to tooth whitening compounds, dental bonding and filling compounds used to fill a tooth after a cavity has been drilled out of the tooth, and adhesives used to bond two objects together, and in particular to apparatus which dispenses tooth whitening compounds used to whiten teeth, apparatus used to dispense dental bonding compounds, and apparatus used to dispense adhesives.

2. Description of the Prior Art

One significant problem with prior art apparatus used to retain and dispense tooth whitening compounds is that they are reused over and over, resulting in the possible transmission of diseases from one dental patient to another.

The following 26 patents and published patent applications are the closest prior art references which were uncovered in the search.

1. U.S. Pat. No. 5,611,687 issued to Eugene C. Wagner on Mar. 18, 1997 for "Oral Hygiene Delivery System" (hereafter the "Wagner patent");

2. U.S. Pat. No. 6,176,632 issued to Hidehei Kageyama et al. on Jan. 23, 2001 for "Liquid Container" (hereafter the "'632 Kageyama patent");

3. U.S. Pat. No. 6,227,739 issued to Hidehei Kageyama on May 8, 2001 for "Liquid Container" (hereafter the "'739 Kageyama patent");

4. United States Published Patent Application No. 2005/0063766 to Sou Y. Chen et al. on Mar. 24, 2005 for "Applicata Pen" (hereafter the "Chen Published Patent Application");

5. U.S. Pat. No. 6,918,515 issued to Yoshio Noguchi on Jul. 19, 2005 for "Liquid Container" (hereafter the "Noguchi patent");

6. United States Published Patent Application No. 2006/0275225 to Michael Prencipe et al. on Dec. 7, 2006 for "Applicator and Method For Applying A Tooth Whitening Composition" (hereafter the "Prencipe Published Patent Application");

7. U.S. Pat. No. 7,201,527 issued to Richard Christopher Thorpe et al. on Apr. 10, 2007 for "Twist Up Pen Type Dispenser With Brush Applicator" (hereafter the "Thorpe patent");

8. United. States Published Patent Application No. 2007/0086830 to Hidehei Kageyama on Apr. 19, 2007 for "Liquid Container" (hereafter the "Kageyama Published Patent Application");

9. United States Published Patent Application No. 2008/0274066 to Robert Eric Montgomery on Nov. 6, 2008 for "Compositions, Methods, Devices, And Kits for Maintaining or Enhancing Tooth Whitening" (hereafter the "Montgomery Published Patent Application").

10. U.S. Pat. No. 7,794,166 issued to Jun Zhang on Sep. 14, 2010 for "Press-Type Cosmetic Container with Anti-Press Means" (hereafter the "Zhang patent");

11. United States Published Patent Application No. 2011/0129288 to Junya Uehara on Jun. 2, 2011 for "Liquid Applicator" (hereafter the "Uehara Published Patent Application");

12. U.S. Pat. No. 7,980,778 issued to Tetsuaki Akaishi et al. on Jul. 19, 2011 for "Liquid Applicator" (hereafter the Akaishi patent");

13. U.S. Pat. No. 8,328,449 issued to James C. Wightman et al. on Dec. 11, 2012 for "Click Pen Applicator Device And Method of Using Same" (hereafter the "Wightman patent");

14. Japanese Patent No. JP096151123A issued to Shiraishi Katsuhiko et al. on Jun. 10, 1997 for "Tooth Coating Liquid" (hereafter the "Katsuhiko Japanese Patent");

15. Japanese Patent No. JP2007130437A issued to Kageyama Shuhei on May 31, 2007 for "Liquid Container" (hereafter the "Shuhei Japanese Patent").

16. U.S. Pat. No. 4,121,739 issued to William David Devaney et al. on Oct. 24, 1978 for "Dispenser With Unitary Plunger And Seal Construction" (hereafter the "Devaney patent");

17. U.S. Pat. No. 5,104,005 issued to Franz K. Schneider, Jr. et al. on Apr. 14, 1992 for "Dual Component Mechanically Operated Caulking Gun" (hereafter the "Schneider patent");

18. U.S. Pat. No. 5,310,091 issued to Walter B. Dunning et al. on May 10, 1994 for "Dual Product Dispenser" (hereafter the "Dunning patent");

19. U.S. Pat. No. 5,333,760 issued to Christen Simmen on Aug. 2, 1994 for "Dispensing And Mixing Apparatus" (hereafter the "Simmen patent");

20. U.S. Pat. No. 5,535,922 issued to Bernard J. Maziarz on Jul. 16, 1996 for "Caulking Gun Dispensing Module For Multi-Component Cartridge" (hereafter the "Maziarz patent");

21. U.S. Pat. No. 6,116,900 issued to Calvin D. Ostler on Sep. 12, 2000 for "Binary Energizer And Peroxide Delivery System For Dental Bleaching" (hereafter the "Ostler patent");

22. U.S. Pat. No. 6,283,660 issued to Patrick J. Furlong et al. on Sep. 4, 2001 for "Pen Dispensing And Cartridge System" (hereafter the "Furlong patent");

23. United States Published Patent Application No. 2009/0095777 to Frank. Francavilla on Apr. 16, 2009 for "Dispensing Pen" (hereafter the "Francavilla Published Patent Application");

24. U.S. Pat. No. 7,748,980 issued to Paul Mulhauser et al. on Jul. 6, 2010 for "Dispenser for Dental Compositions" (hereafter the "Mulhauser patent");

25. U.S. Pat. No. 7,882,983 issued to Dean K. Reidt et al. on Feb. 8, 2011 for "Capsule for Two-Component Materials" (hereafter the "Reidt patent");

26. U.S. Pat. No. 8,096,449 issued to Wilheilm A. Keller on Jan. 17, 2012 for "Dispensing Appliance for a Multiple Cartridge" (hereafter the "Keller patent").

The Wagner patent discloses:

"A delivery system for a liquid oral hygiene preparation suitable for tooth whitening, tooth cleansing and the treatment of. The delivery system includes an elongate band shaped body. A supply of the hygiene preparation saturates a fibrous wadding carried in a hollow chamber of the body. At an end of the body, an applicator formed of felt or synthetic fibers is seated. The applicator includes a broad tip and a stem wick which is received in the wadding and draws the preparation to the tip by capillary action. The preparation is applied to tooth surfaces, oral lesions, and the like by pressing the tip against the surface to receive the preparation and, where appropriate, wiping the tip along the surface. In an alternate embodiment, ball applicator is provided and the hygienic preparation may be carried in the chamber without the wadding."

The '632 Kageyama discloses:

"A liquid container such that the liquid received in it will not easily spring out from its tip even if it is wrongly operated, comprises a tank portion for receiving a liquid, a knock bar stretching axially movably within the tank portion which is designed to have on its axial tip portion a pump shelf portion whose diameter have been enlarged, an induction bar fixed into the tip of the knock bar, a brush provided on the tip side of the induction bar, and a spring for always energizing the above knock bar and induction bar rearward. On the internal periphery surface of the above tank portion, a plurality of ribs are formed which stretch axially and on top of which the above pump shelf portion can slide, the internal periphery surface ahead of the ribs is at the same level as and continuous with the top face of the ribs and designed as a diameter-reducing portion where the pump shelf portion can slide. The pump shelf portion slidably touches the ribs when it is not biased."

The '739 Kageyama patent is related to the previously discussed patent and discloses: "A liquid container includes a body having a tank portion housing liquid, and a liquid supply port at a front side thereof, a piston moving forward inside the tank portion, a piston rod being integrally connected to the piston and extending rearward, the piston rod having an external thread formed in a periphery thereof, an operation cylinder being attached to a rear part of the body in a relatively rotatable fashion, a piston rod guide being adapted to be rotated integrally with the operating cylinder, the piston rod guide having an internal thread hole which is engaged with the external thread of the piston rod, and a ratchet cylinder being fixed in the rear inside the body, the ratchet cylinder having a bore through which the piston rod is pierced in a relatively unrotatable fashion. The operation cylinder is formed with serrated gear teeth at a front end thereof, and the ratchet cylinder is formed with a ratchet gear tooth which is brought into engagement with the serrated gear teeth and adopted to be selectively protruded or retracted in an axial direction, at a rear end thereof."

The Chen Published Patent Application discloses:

"FIG. 1 is a cross-sectional view of an applicator pen 100 according to a first embodiment. The applicator pen 100 is formed of a number of different sub-assemblies that are then combined in an engaging manner to fowl the applicator pen 100. More specifically, the applicator pen 100 includes a body 110 and an applicator assembly 200 that serves to restrict and disperse an applicator material 112 that is stored within the body 110. The applicator pen 100 also includes a drive mechanism 300 for advancing the applicator material 112 within the body 110 such that it is introduced into and dispersed through the applicator assembly 200 to the consumer. The drive mechanism 300 is coupled to a button assembly 400 that permits the consumer to simply advance the applicator material 112 an incremental amount within the body 110 upon manipulation of the button assembly 400, e.g., a press and release action of the button assembly 400.

While the applicator material 112 can be any number of different types of materials, it will be appreciated that one exemplary use of the applicator 100 is as a cosmetic applicator and therefore, in this particular use, the applicator material 112 is in the form of a cosmetic product. For example, the applicator material 112 can in the form of conventional make-up, such as an eye shadow or liner, lipstick, other facial products, etc. The applicator material 112 is typically a viscous material, such as a liquid, gel or other material that has some flow properties."

The focus of this Chen Published Patent Application is primarily a cosmetic applicator for eyeshadow, a liner, etc. and not for teeth whitening.

The Noguchi patent discloses:

"In a liquid container, the dimension of inside diameter of a liquid supply portion is not subject to any restriction, and also a liquid leakage suppressing mechanism that is not subject to any restriction by the viscosity of stored liquid is provided. A liquid container includes a body having a tank for storing a liquid; a supply mechanism which is connected to the tip end portion of the body and has a brush for supplying the liquid; and a drive mechanism for pushing out the liquid L in the tank T to the supply mechanism. A valve which is normally closed and can be opened only when the drive mechanism is operated is provided between the tank and the supply mechanism."

The Prencipe Published Patent Application discloses:

"The dispenser 10 is shown as a complete unit in FIGS. 1 and 2. The dispenser is comprised of three sections. These are an applicator section 12, a whitening product storage section 14 and a dispenser drive section 16. The applicator section is comprised of an overcap 18, an applicator surface 30, an applicator surface holder 32, an applicator mounting unit 36 and a delivery channel 34. The whitening product in product chamber 40 is delivered to the applicator surface through delivery channel 34. A tubular wall 20 forms the product chamber 40. Piston 42 forms the upper wall of product chamber 40.

The dispenser drive section 16 is comprised of the mechanism to advance piston 42 downward in whitening product chamber 40. This dispenser drive section is shown in more detail in FIG. 5. Rotating unit 22 will rotate while tubular wall 20 of the whitening product chamber is stationary.

FIG. 7 shows an applicator tip with a fibrillated surface The applicator tip is comprised of channel 60 having a cross-section 65 which receives the peroxide containing tooth whitening composition from storage chamber 40. Fibrillated surface 62 is the application surface to apply the composition to the teeth. The peroxide tooth whitening composition flows through opening 64 of the channel 60. Applicator surface holder 66 holds channel 60 and is in turn held in place by applicator mounting unit 68. FIG. 8 is an exploded view of the applicator tip of FIG. 7. Additionally shown in this view is a chamber 70 on the applicator surface holder channel 72 of the applicator mounting unit 68. Flange 74 holds the applicator surface holder 66 in applicator mounting unit 68."

The Dwyer Published Patent Application discloses:

"A method for manufacturing a cosmetic product applicator assembly includes selecting a disposable handle having a desired design from a number of handles of various designs. Each of the handles includes an elongated, decorative housing with a first end having an opening, a hollow chamber extending from the opening into the housing, and a flattened portion for displaying a word, phrase, symbol or design. A cosmetic product applicator having a first terminal end from which the cosmetic product is dispensed and a second terminal end opposite the first terminal end is inserted into the handle. The hollow chamber is adapted to receive and engage the second terminal end of the applicator in a non-rotatable manner."

The Thorpe patent discloses:

"As shown in FIGS. 2 and 5, the twist up pen type dispenser with brush applicator 1 comprises a body 2, preferably substantially in the shape of a cylinder, having a top 3, a bottom 4, an outer surface 5 and an inner surface 6 which defines an annular space 7. As shown in FIGS. 4 and 5, material 8 may be within the annular space 7, which functions as a reservoir for the material 8 within the twist up pen type dispenser with brush applicator 1. The material 8 may be a dentifrice, such as tooth gel, tooth paste, mouthwash, mouth rinse, tooth whitener and combinations thereof, cosmetics, such as mascara and eyeliner, hair colorants such as darkeners, like darkeners for facial hair such as moustaches, dyes or similar materials, or skin treatment compositions, combinations thereof, and the like."

The Kageyama Published Patent Application discloses:

"To provide a liquid container which includes a liquid supply member that is exchangeably mounted thereto and prevents liquids in liquid supply members from being mixed each other after exchanging the liquid supply members. The liquid container is provided which includes a container body with a tank section to hold a liquid, an applicator coupled to the front end of the container body, a piston which is advanced through the tank section, and a piston advancing mechanism which has a pushing member and causes the piston to be advanced through the tank section in response to the operation of the pushing member. The applicator is removably coupled to the container body, and the piston advancing mechanism causes the piston to be moved only forward."

The Montgomery Published Patent Application discloses:

"The first and/or second tooth whitening compositions are preferably disposed in a delivery device 10 (e.g., FIGS. 2-4, 9, and 10), such as a dispensing tube, pencil, pen or liquid stick having an applicator 12, such as a felt tip 14 (FIG. 3), brush 16 (FIG. 4), roller ball, or non-woven pad. In one embodiment, the delivery device 10 includes more than one applicator 12 that may be removably engaged with the device 10. In an embodiment wherein the device 10 is a pen or a pencil, the applicator 12 may be retractable and/or housed in a cap 18. The tooth whitening compositions of the present invention may be housed directly within a reservoir 20 in the device 10 or may be supplied in a removable cartridge (not shown) within the reservoir 20 that may be replaced or refilled. The delivery device 10 may dispense the tooth whitening composition through a transfer channel 21 through capillary action, such as in a flow through pen, or through an actuator 22, such as mechanical piston with a click mechanism, twist button and ratchet mechanism, or push button mechanism, or through a vacuum method of ejection, or through other such mechanical means for transferring the composition from the device to an oral cavity surface in need of treatment. The actuator 22 may be present on first end 24 of the device 10 and the applicator on a second end 26 of the device 10 or the actuator 22 may be present on a side wall 28 of the device. In one embodiment, the delivery device 10 includes a felt tip 14 or brush 16 applicator 12 wherein the inventive composition is dispensed to the applicator 12 through actuation of the actuator 22, such as by a clicking or twisting mechanism. Kotobuke Pencil, Japan, is one manufacturer of such types of delivery devices 10 (see, e.g., U.S. Pat. No. 6,176,632)."

The Zhang patent discloses:

"The present invention is related to a press-type cosmetic container with an anti-press means. That is, a cosmetic container adopts the way of pressing to output the material therein. More particularly, the press cover of the cosmetic container is stopped by a block to prevent discharging or leaking the material in the cosmetic container."

Claim 1 of the Zhang patent reads as follows:

"A press-type cosmetic container with an anti-press means comprising: a tube member having a sleeve at the one end thereof, the outer edge of the sleeve being disposed a collar base; a rotating tube member being disposed a female ringing slot at the inner edge of the one end thereof, the rotating tube member being female-connected to the outer edge of the sleeve and the collar base of the tube member being slid on the female ringing slot so as to make the rotating tube member be turned around on the sleeve, wherein two axial extending ribs are disposed at the inner wall of the another end of the rotating tube member, a block is disposed between the two ribs, and a resisting member is disposed beside the two ribs; a press cover having two wedging member being extended outwardly and disposed on the two side edges thereof respectively, the one end of the press cover located at the wedging member being embedded at the inner edge of the free end of the rotating tube member, and the one wedging member being disposed beyond the two ribs; herein the block stops pressing the press cover in order to stop outputting material in the cosmetic container and then achieve the function of preventing improper pressing, and the rotating tube member is then turned around, the two wedging members are moved to locations beside the resisting member so as to output the material."

The Uehara Published Patent Application discloses:

"The present invention is a liquid applicator which, in its assembled state an applying part, joint, and front barrel are fixed to a barrel body front end portion, the step of an indented/projected engaging portion on the inner peripheral side of the applying part rear end portion is abutted from behind against and engaged with the step of an indented/projected engaging portion on the outer peripheral side of the forward part of the joint. At the same time, an indented/projected engaging portion on the outer peripheral side of the applying part rear end portion is abutted against and engaged with an indented/projected engaging portion on the inner peripheral side of the front barrel's forward part, and an indented/projected engaging portion on the inner peripheral side of the front barrel rearward part is engaged with an indented/projected engaging portion on the outer peripheral side in the rearward part of joint, whereby applying part, joint and front barrel are formed so as to fix the applying part to barrel body by means of the joint and the front barrel."

The Akaishi patent discloses:

"A liquid applicator includes a liquid pressing mechanism 6 for pressurizing an application liquid 4 inside a main body 2 so as to supply the application liquid to an applying member 10 at the front end by the pressing of liquid pressing mechanism 6, wherein the applying member 10 is made of an elastic material, has a valve structure 8 which is formed with a communication path 24 for communication between the inside and outside of main body 2 and can close the communication path 24 by elasticity in the normal condition and open the communication path 24 by elastic deformation of the communication path when the application liquid is pressurized by liquid pressing mechanism 6, and, an ejection opening 24a of communication path 24 of valve structure 8 is arranged to front onto the applying portion 10a of the applying member 10."

The Wrightman patent discloses:

"A click pen applicator device that provides predetermined dosing of the formulation for precise application, and rapidly primes the formulation using the dosing click mechanism to prepare the applicator for use."

Claim 1 of the Wrightman patent reads as follows:

"A device for dispensing a formulation comprising: a centerband having a proximal end and a distal end and defining a storage section having the formulation disposed within; an applicator section situated at the distal end of the centerband; and a multistage actuator section situated at the proximal end of the centerband for rapid priming with a click dispensing mechanism with a piston seat having two sets of external threads on a shaft with an unthreaded length therebetween."

The Katsuhiko Japanese Patent discloses:

"PROBLEM TO BE SOLVED: To obtain a coating liquid capable of coloring tooth or tooth crowns to white or any other color by using an acrylic resin prepared by neutralizing an acrylic ester-methacrylic eater-based copolymer with a specific compound. SOLUTION: This tooth coating liquid contusions ethanol and an acrylic resin prepared by neutralizing an acrylic ester-methacrylic ester-based copolymer with 2-amino-2-methyl-1,3-propanediol or 2-amino-2-methyl-1-propanol, and may also contain a color pigment or extender pigment, and furthermore, ceramic(s) and/or a vinyl acetate resin. It is preferable that this coating liquid comprises 10-94.8 wt. % or more of ethanol, 0.1-30 wt. % of a pigment, 0.1-20 wt. % of the above acrylic resin, and 5-30 wt. % of ceramic(s) and/or butyl acetate resin. The pigment is pref. titanium dioxide (optimally, ≤100 nm primary particle diameter on average)."

The Shuhei Japanese Patent discloses:

"PROBLEM TO BE SOLVED: To provide a liquid container which includes a liquid supply member that is exchangeably mounted thereto and prevents liquids in liquid supply members from being mixed each other before and after exchanging the liquid supply members; SOLUTION: The liquid container includes a container body 12 with a tank section T to hold a liquid, an applicator 20 coupled to the front end of the container body 12, a piston 22 which is advanced through the tank section T, and a piston pressing mechanism 23 which has a knocking member 32 and causes the piston 22 to be pressed through the tank section T in response to the operation of the knocking member 32. The applicator 20 is removably coupled to the container body 12, and the piston pressing mechanism 23 causes the piston 22 to be moved only forward."

The Devaney patent discloses:

"A dispenser for precisely metering viscous fluids from a cartridge. The dispenser includes a cartridge body and a plunger having a piston head at its extremity. The plunger is unitarily configured from a plastic material, including seal rings in the piston head. Each piston head including two such seal rings axially spaced from one another and configured to include sharp peripheral edges permitting resilient wedging contact within the bore of the cartridge."

The Schneider patent discloses:

"A dual component caulking gun which utilizes a gun body to which there is affixed a dual component cartridge assembly designed to carry dual component cartridges. A ball screw is journaled within the gun body for rotary motion but locked against axial motion and extends in a direction opposite the component cartridge assembly. A pair of ram rods are journaled through the gun body and terminate at the first end in ejector rams and at their opposite end in a transfer bar that is interconnected to the ball screw by means of a ball screw nut"

The Dunning patent discloses

"A dispenser for simultaneously dispensing and mixing a pair of fluid products such as chemically reactive resins, from a pair of axial adjacent front and rear chambers. A piston is mounted within each of the chambers and is moveable with respect to the hollow interior of the respective chamber for dispensing the fluid product therefrom. Telescopic movement of the rear chamber within the front chamber moves the pistons synchronously through the chambers to provide for controlled discharge of the products through a front discharge nozzle. A fixed hollow delivery tube extends through the interior of the front chamber and telescopically receives therein a post which is mounted on a rear wall of the rear chamber. The rear chamber has a relatively tight sliding fit within the front chamber so that a partial vacuum is formed within an annular space which forms between the two pistons as they move apart upon discharge of the two products to produce a "suck back" effect on product remaining in the discharge nozzle."

The Simmen patent discloses:

"A dispensing and mixing apparatus for simultaneously dispensing from a cartridge into a static mixing element components which harden when mixed. The components exit the cartridge into the mixing element without intermixing as the components leave the cartridge. The initial intermixing of the components takes place within the mixing element. The cartridge is reusable since the components do not become mixed and harden as they come out of the cartridge. The chambers in the cartridge are of semi-cylindrical configuration and have rounded corners. Ribs can be provided on the cartridge for stiffening the cartridge from deforming under extrusion."

The Maziarz patent discloses:

"The invention provides a dispensing module for dispensing multi-part adhesive from a multi-component cartridge utilizing a standard caulking gun. The dispensing module comprises a piston actuator and a module housing which when assembled with a standard multi-component cartridge and inserted into a standard caulking gun allows the components from the multi-component cartridge to be dispensed."

The Ostler patent discloses:

"A dental bleach storage, mixing and delivery device and related method are disclosed. The device includes a barrel with at least two chambers. The chambers store components that when mixed can form a dental bleach or whitener. A plunger is provided that can be reciprocated within the barrel to force such components from their chambers. A mixing tip is provided for the end of the barrel. The components may be forced through the mixing tip which thoroughly mixes them together. The resulting bleach or whitener is applied to a patient's teeth where oxygen ions released from the bleach or whitener and will whiten the patient's teeth."

The Furlong patent is a pen dispensing cartridge system which issued in 2001 and is still in full force and effect. The patent discloses:

"The present invention features a pen used, for example, to dispense nail polish for finger nail application. The design is for a unit of use, meaning that the preferred pen uses cartridges, i.e., units. In a preferred embodiment, each cartridge is filled with polish and has a brush head. After the cartridge is used, the user simply disposes of the old cartridge and replaces it with a new cartridge for the next application."

The Francavilla discloses:

"The present invention is related to a dispensing device. The dispensing device includes a container; a dispensing opening located at one end of the container; a plunger located inside the container; a push button associated with the plunger; and a drive mechanism configured to drive the plunger linearly inside the container from a first position towards the dispensing opening when the push button is pressed and to hold the plunger at a second position, wherein the second position is closer to the dispensing opening than the first position."

The Reidt patent discloses:

"Capsule (10) for two or more components of a material which are to be mixed together, comprising a cartridge (11) comprising an outlet (12), a first component chamber (13) for containing a first component, and a second component chamber (14) for containing a second component, the two chambers (13, 14) opening into the outlet (12); and a piston (15)

which at least with its front end sits in the cartridge (11), lies with its rear end outside the component chambers (13, 14) and, when it is pushed forwards, presses the two components out of their component chambers (13, 14)."

The Mulhauser patent discloses a dispenser for dental compositions.

Claim 1 of the Mulhauser patent reads as follows:

"An apparatus for dispensing dental compositions, the apparatus comprising: a) a body comprising a top shell portion, a bottom shell portion, and a chamber received therein; b) a replaceable cartridge having at least two lumens with at least two pistons, the cartridge operable to dispense a component of a dental compound contained within the lumens, and wherein the cartridge is further operable to be at least partially inserted into the chamber; c) an inner mechanical system disposed in the body, the inner mechanical system comprising a rack system, said rack system having at least two racks operable to be urged forward to engage a piston in each lumen of the cartridge; d) a button system in contact with the body, the button system operable to be depressed in a direction substantially forward and in line with the rack system by a user such that the button system engages the inner mechanical system when depressed, such that the rack is advanced a predetermined distance such that a metered amount of the components of the dental compound is dispensed from the at least two lumens; and e) wherein the inner mechanical system further comprises a plurality of teeth disposed on the rack system, and a drive spring and a pawl spring disposed on the body, the drive spring and the pawl spring being operable to interface with at least one of a plurality of teeth on the rack system and at least one surface of the button system such that depression of the button system by a user initiates drive spring to advance the rack system a predetermined distance proportional to the distance between a first selected tooth located on the rack and a second selected tooth located on the rack and initiates the pawl spring to disengage from a third selected tooth on the rack and engage a fourth selected tooth on the rack located at a distance substantially equal to the distance between the first tooth and the second tooth, and release of the button causes the drive spring to disengage from said first selected tooth and engage the second selected tooth on the rack."

The Keller patent discloses a dispensing appliance for a multiple cartridge. The broadest claim is Claim 1 which reads as follows:

"A dispensing appliance for a multiple cartridge or syringe, comprising: a housing configured to receive the multiple cartridge or syringe, and wherein the housing has a housing thread and a rotatable portion that has a complementary thread, wherein the housing thread and the rotatable portion cooperate in such a manner that by a mutual rotation of the housing thread and the rotatable portion, the rotatable portion is continuously displaceable relative to the housing in a dispensing direction, wherein the housing is configured to receive the multiple cartridge or syringe having at least two adjacent and parallel storage containers, wherein a thrust force of the rotatable portion is transmitted to a multiple ram with a single thrust plate, and wherein the multiple ram slides in the at least two adjacent and parallel storage containers of the multiple cartridge or syringe and the thrust plate is non-rotatably guided inside the housing."

There is a significant need for an improved apparatus to dispense compounds including but not limited to tooth whitening compounds where the tooth whitening compounds are dispensed from a new and unused retainers.

There is also a significant need for an improved apparatus to dispense dental bonding compounds from new and unused retainers and adhesive compounds from new and unused retainers.

SUMMARY OF THE INVENTION

The present invention involves the field of numerous types of compounds including tooth whitening compounds and in particular, to specific apparatus which are used to retain tooth whitening compounds and then dispense them either into a dental tray where the tray is placed over the patient's teeth for a period of time or the tooth whitening compound is directly applied to the patient's teeth by the dentist or the dental assistant. More broadly described, the present invention includes compound and applicators used to dispense the compounds including tooth whitening compounds, dental bonding and filling compounds, adhesives, finely ground powder, jells, creams and paints (which are hereafter jointly referred to in this patent application as a "compounds").

Although the summary discussed below relates to tooth whitening compounds in detail, it is understood that the present invention includes all products defined above as compounds and is not limited to tooth whitening compounds.

The present invention involves a pen which removably retains a single use capsule containing tooth whitening compounds and removably retains disposable tooth whitening applicators. One of the major problems with prior art tooth whitening applicators is that the applicator itself is reused over and over again through syringes which contain the tooth whitening compound and even though they are sterilized, run the risk of transmitting disease from one patient to another. Therefore, there is a significant need for an improved tooth whitening apparatus where the capsule containing the tooth whitening compound or compounds is disposable and replaceable with a new clean capsule with a fresh supply of tooth whitening compound or compounds and the applicator heads which are used to apply the compounds to teeth or to a dental tray are also disposable and replaced with new applicators so that the patient receives a completely new and sterile system for the purpose of applying tooth whitening compounds. The only portion of the apparatus which is reused is the retaining pen which is used to removably retain the tooth whitening compound and to removably retain the tooth whitening applicators.

One embodiment of the present invention involves a uni-dose single use cartridge or capsule which contains tooth whitening compound in a sealed condition with a cap that has an opening which is sealed by a frangible opening which seals the capsule until it is ready for use and a screw on cap which contains at a remote end a piercing object to pierce the frangible seal so that the tooth whitening compound can be dispensed from the capsule.

In one preferred embodiment, the capsule contains a dividing wall which separates the interior of the single use capsule or cartridge into two chambers where the compounds are separated from each other and do not come in contact until they are dispensed from the front end of the capsule and then enter a mixing chamber where the two compounds are mixed together to activate them and thereafter, dispensed from the applicator head to the dental tray or directly onto the patient's teeth.

The chamber contains a dual plunger which moves the compound forward by a unique ratchet mechanism contained within the pen, which mechanism causes a pair of plungers to engage separate rear pockets of the rear plunger to move the plunger forward in increments until the desired amount of compound is released from the capsule and mixed into a mixing tip which then flows directly into an applicator head.

Further, the amount of separate compounds can either be in the same amount by having the dividing wall of one thickness so that the interior chamber of the capsule is the same on each side or alternatively, the dividing wall can be thicker by several increments along one side so that the amount of one compound in the smaller side is less than the amount of the other compound if that is the formula that is required for appropriate mixing so that one portion of the compound may be half or a third of the second compound and that would be the appropriate mixing formula when they are mixed together.

The invention includes the plunger which also acts as a rear seal to prevent the compound from exiting the rear of the retaining capsule or cartridge and has two spaced apart pockets at the rear end of the plunger to respectively receive a respective one of a pair of pistons from the moving ratchet mechanism contained within the dispensing pen.

In an alternative embodiment, the cartridge does not contain any dividing wall and simply has one interior chamber which contains a single compound that does not need to be mixed with any other compound to be activated and contains a plunger which encapsulates the entire interior at the rear end of the rear chamber and is moved forward with a single piston from the dispensing pen, also moved forward through a ratchet mechanism so that the piston pushes the plunger in desired increments so that the tooth whitening compound can be dispensed from the front of the removable and replaceable cartridge in desired increments. In this case it is not necessary to have a mixing tip since there is no mixing required of the compound and the front of the capsule is directly applied to the tooth applicator.

In the embodiment where there is a dual chamber, the compound retaining capsule or cartridge has a threaded front end and the mixing tip has engaging threads which are screwed onto the threads of the dual chamber compound retaining capsule and before threading the mixing chamber onto the compound retaining chamber, the frangible seal is penetrated by the sharp object on the front of the cap and then the mixing tip is threaded onto the threads of the dual tooth whitening compound capsule and when compound is dispensed from the capsule, it is mixed in the mixing tip. A tooth applicator is then threaded onto the threaded end of the mixing tip so that the mixed compound can then flow through the applicator either into a dental tray where the compound is placed over a person's teeth or alternatively, directly applied to a person's teeth either through a glove hand rubbing or alternatively, through an applicator brush which is also part of the present invention.

In the case of the single chamber tooth whitening compound retaining capsule, the dispensing tip is directly threaded onto the threads of the opened chamber and the tooth whitening compound is directly applied into the dental tray or directly onto the patient's teeth.

With respect to alternative embodiments of the applicators, one embodiment is a straight applicator which is generally frustum shaped having a narrow dispensing tip and a threaded end which is threaded onto either the threaded end of the mixing tip or a threaded end of the cartridge and through which the tooth whitening compound flows and can be placed either into a dental tray or onto a patient's teeth.

In an alternative embodiment of the applicator, the applicator is horn-shaped or bent so that the tooth whitening compound can be directly applied to locations in the patient's mouth where teeth are near the back of the mouth, either upper or lower teeth and usually on the exterior but if necessary, also on the top or interior of the tooth.

In an alternative embodiment of the applicator, the applicator has an opening with a brush so that the tooth whitening compound extends through the applicator opening and then the brush is used to apply the tooth whitening compound onto the patient's tooth.

It is a primary object of the present invention to provide a reusable capsule and reusable applicator so that tooth whitening compounds which are contained in the capsule are used only once and the applicators used to apply the tooth whitening compound are also used only once and then discarded and replaced with a separate tooth whitening compound retaining capsule or cartridge and also replaced with separate applicator heads.

It is a further object of the present invention to provide a reusable cartridge or capsule which contains a single compound which does not need to be mixed with any other compound and can simply be dispensed once the sealed capsule or cartridge is opened to dispense the tooth whitening compound onto teeth or onto a dental tray where it can be used.

It is a further object of the present invention to provide a removable capsule which has a dividing wall so that the capsule contains two separate compounds which are separated from each other and which may either have equal amounts of compounds on either side of the dividing wall or different amounts of compound where one compound is less than the other compound depending upon the formulation required for that tooth whitening application and then the compounds are mixed when they enter a chamber for mixing purposes.

It is the primary object of the present invention to provide a non-reusable container and non-reusable applicator head so that a fresh container containing fresh tooth whitening compounds, fresh dental bonding and filling compounds and adhesive compounds and fresh new applicators are used every time a new compound is dispensed so that a compound is not reused from one patient to another or from one adhesive bonding application to another, thereby providing safety and health to subsequent patients and products.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
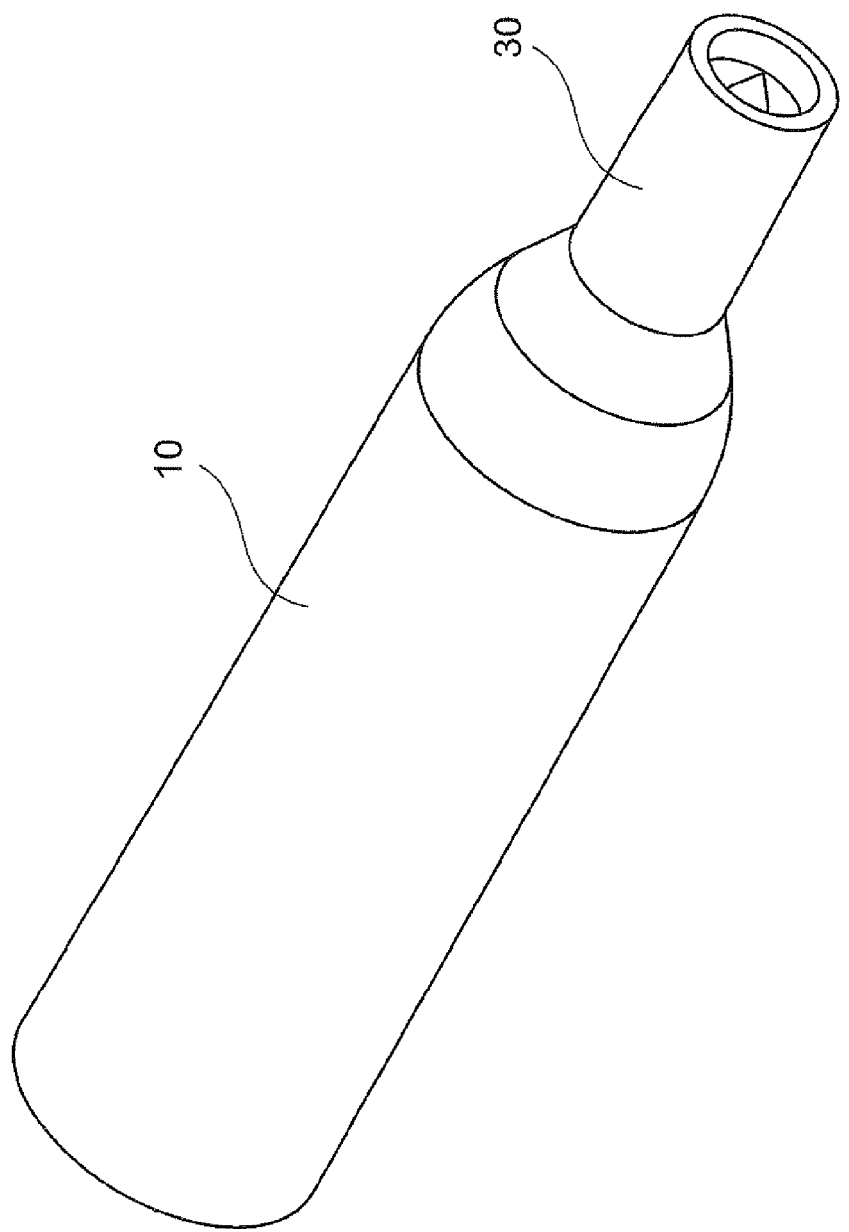
FIG. 1 is a top perspective view of the a unidose single use cartridge which contains compounds selected from the group consisting of the tooth whitening compounds, dental bonding and filling compounds, adhesive compounds, jells, creams, adhesives and other materials ground into finely ground powders, (jointly and severally defined as "compounds" and in a sealed condition with the cap threadedly retained onto the cartridge, and which cartridge is disposed of and replaced with a new single use cartridge for subsequent application of one of the selected compounds.

Referring to FIG. 1, there is illustrated a top perspective view of the unidose single use cartridge 10 which contains a compound as defined above including compound selected from the group consisting of a tooth whitening compound, a dental bonding and filling compound, and an adhesive compound in a sealed condition with the cap 30 threadedly retained onto the single use cartridge 10, and which cartridge is disposed of and replaced with a new single use cartridge for subsequent application of a compound.

Figure 2:
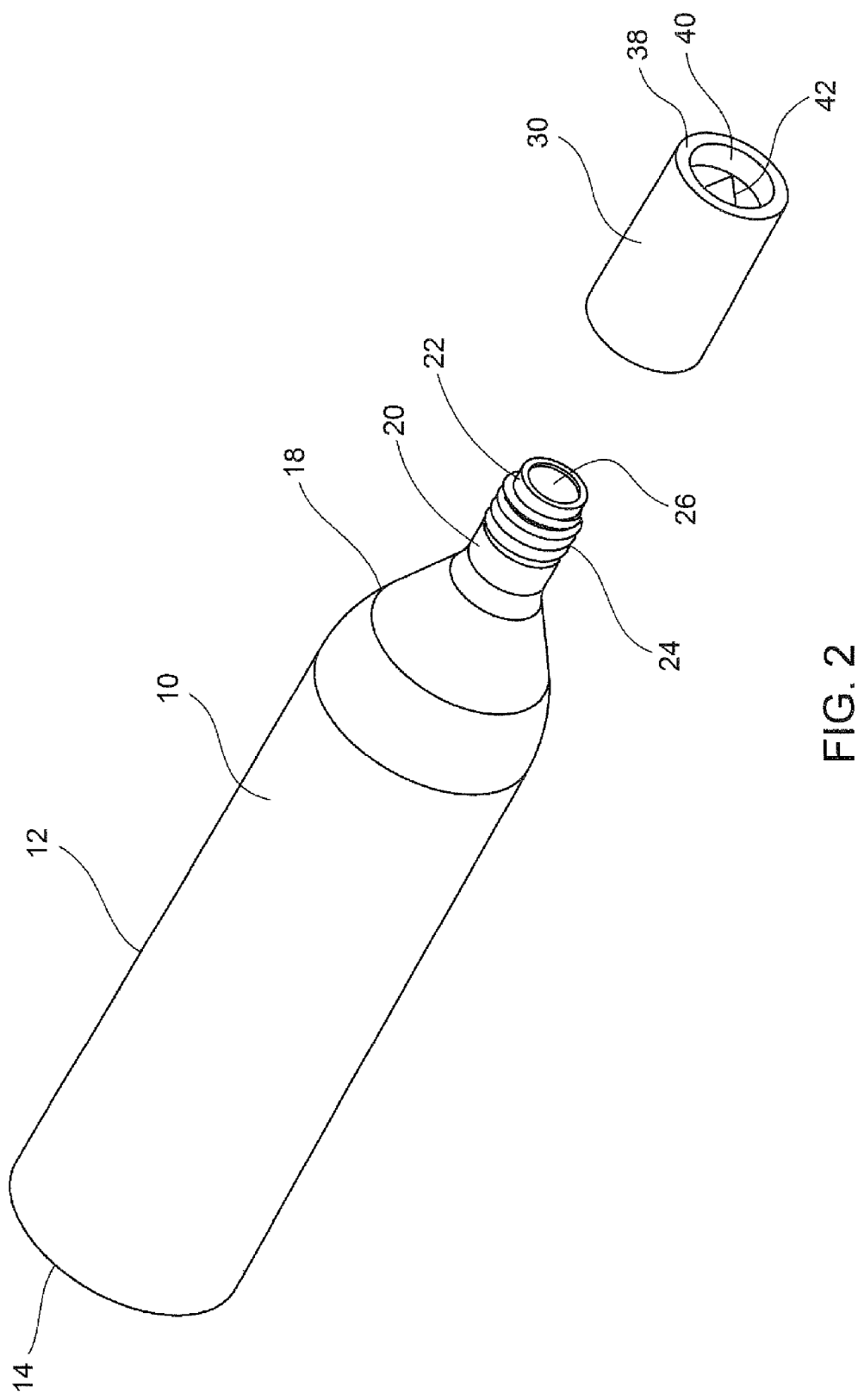
FIG. 2 is an exploded top perspective view of the unidose single use cartridge illustrated in FIG. 1 with the sealing cap removed to expose the front frangible seal on the cartridge.
Figure 4:
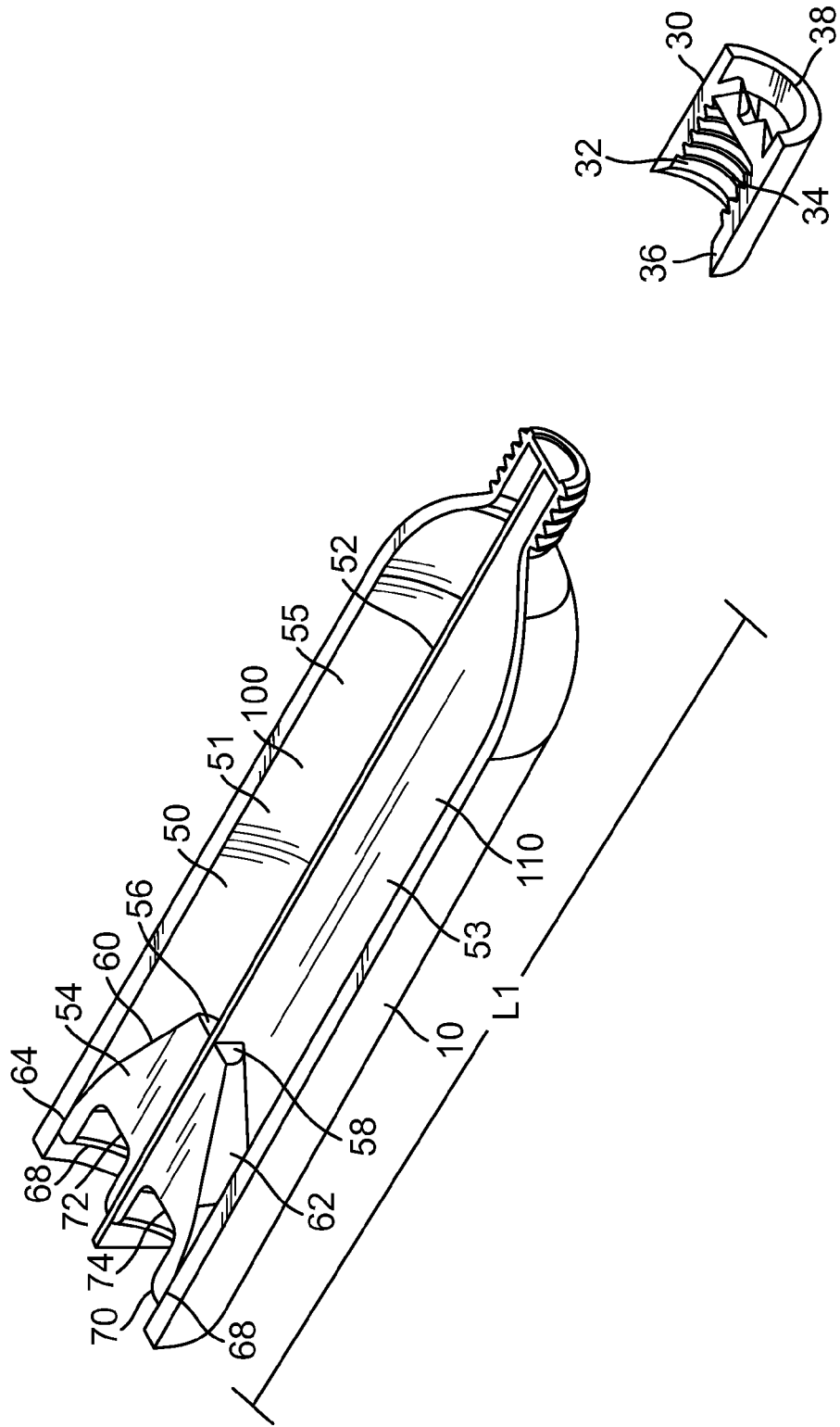
FIG. 4 is a top cutaway view of a first embodiment of the unidose single use cartridge illustrating the divided interior chamber which retains two separate compounds which are separated from each other while in the cartridge by a dividing wall, and a rear plunger having opposing interior faces to push a compound in a respective portion of the interior of the cartridge forward and out of the cartridge, and a pair of opposed angular sidewalls ending in a rear wall forming a seal against the interior sidewall, each rear end of the plunger having a pocket to receive a respective pushing piston.

FIG. 2 is an exploded view showing the same capsule illustrated in FIG. 1 but with the sealing cap 30 removed. In examining FIGS. 1 and 2, the compound single use capsule or cartridge (the term capsule or cartridge are used interchangeably) contains an exterior surface 12 which is generally cylindrical in shape and a rear surface 14 which is generally flat with an opening 16 (see FIG. 7), a front surface 18 which is generally frustum shaped extending from the body of the cylinder 12 to a nozzle having a cylindrical surface 20 extending from the frustum 18 and extending to a dispensing nozzle tip 22 having threads 24 on the exterior surface and a frangible seal 26 on the front end of the tip 22. As illustrated in FIG. 4, the sealing cap 30 is cylindrical with an interior surface 32 with threads 34 adjacent the rear 36 of the sealing cap 30 and a front end 38 with an interior chamber 40 having a piercing tooth 42 (See FIG. 2) within the interior 40 which extends inwardly from the front end 38 of the sealing cap 30. In use, after the cartridge 10 is placed in the tooth whitening pen as will be discussed, the front or tip 22 of the tooth whitening cartridge 10 extends through an opening in the pen and the threaded cap 30 which is previously unscrewed from the threads 24 of the capsule 10 before the capsule or cartridge 10 is inserted into the pen, and the sealing cap 30 is then rotated 180 degrees so that the sharp tooth 42 penetrates the frangible seal 26 so that the tip 22 is opened and a selected compound can therefore be dispensed from the interior of the cartridge or capsule 10.

Figure 3:
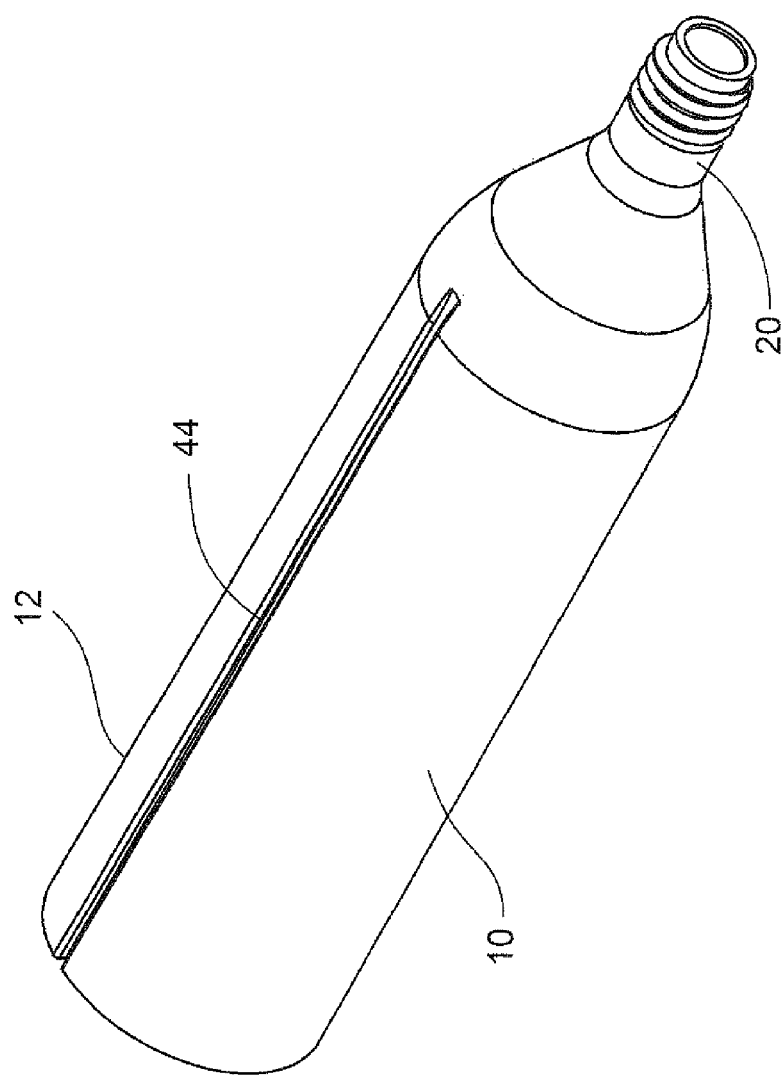
FIG. 3 is a bottom perspective view of the unidose single use cartridge illustrated in FIG. 1 with the sealing cap removed and illustrating the anti-rotation slit in the bottom of the sidewall of the cartridge.

Referring to FIG. 3, there is a bottom perspective view of the unidose single use cartridge 10. The difference between the top view and the bottom view is that bottom view shows an anti-rotation slit 44 in the bottom of exterior surface 12 of the exterior wall 12 of the tooth whitening retaining cartridge 10. The slit 44 does not extend so deep that it goes into the interior chamber as will be discussed. The purpose of the anti-rotation slit 44 is to be inserted into a mating member in the pen to prevent the cartridge 10 from rotating once it is placed into the pen.

Referring to FIG. 4, there is illustrated a top cutaway view of a first embodiment of the unidose single use cartridge 10 containing the divided interior chamber 50 which retains two separate compounds 100 and 110 which are separated from each other while in the cartridge by a dividing wall 52, and a rear plunger 54 having opposing interior faces 56 and 58 to push a compound 100 or 110 in a respective portion of the interior 50 of the cartridge forward and out of the cartridge 10, and a pair of opposed angular sidewalls 60 and 62 ending in rear wall sidewalls 64 and 66 forming a seal against the interior sidewall 51 of the cartridge, each rear end 68 and 70 of the plunger 54 having a pocket 72 and 74 to receive a respective pushing piston from the retaining pen. Referring to FIG. 4, it can be seen that the chamber 50 is divided into two equal chambers 53 and 55 which contain different compounds which cannot come in contact with each other because the dividing wall 52 extends for the varying diameter and Length "L1" of the interior chamber 50 of the cartridge 10. For dual compounds where less is need of one of the two compounds, the dividing wall 52 is thicker on one side to reduce the volume of compound in the smaller chamber, the design of the plunger is modified to accommodate the revised sidewall 52.

Figure 5:
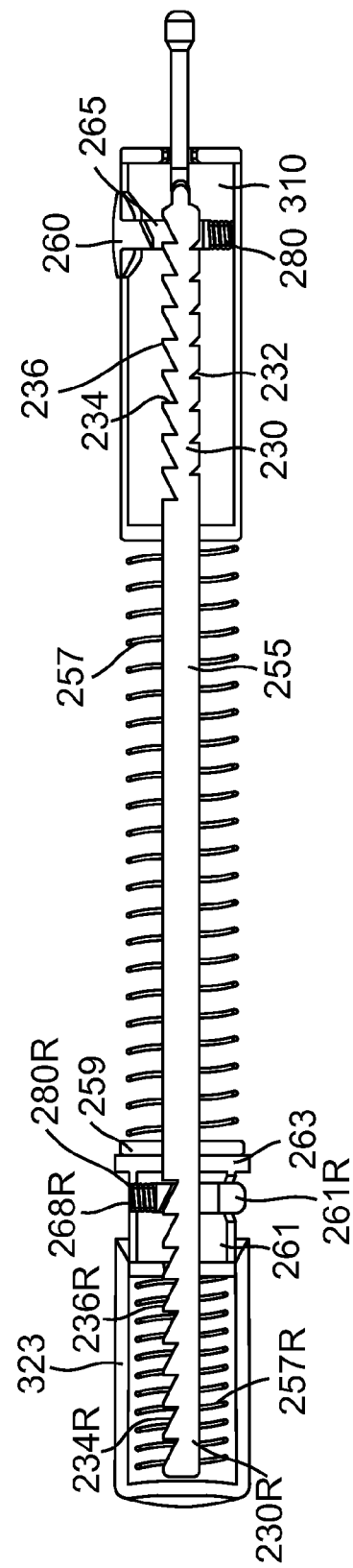
FIG. 5 is a side view of the entire operating mechanism for the divided interior chamber single use cartridge illustrated in FIG. 4.
Figure 7:
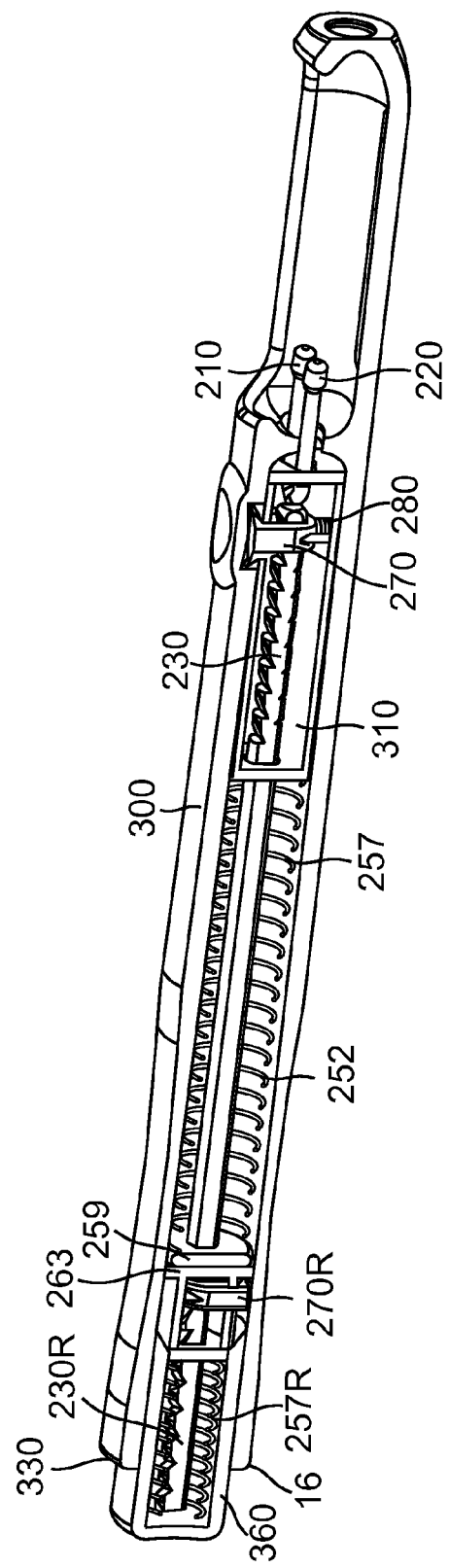
FIG. 7 is a longitudinal cut away side perspective view of the pen of the present invention to illustrate the how the operating mechanism illustrated in FIG. 5 is operationally inserted into an interior chamber of the pen.
Figure 8:
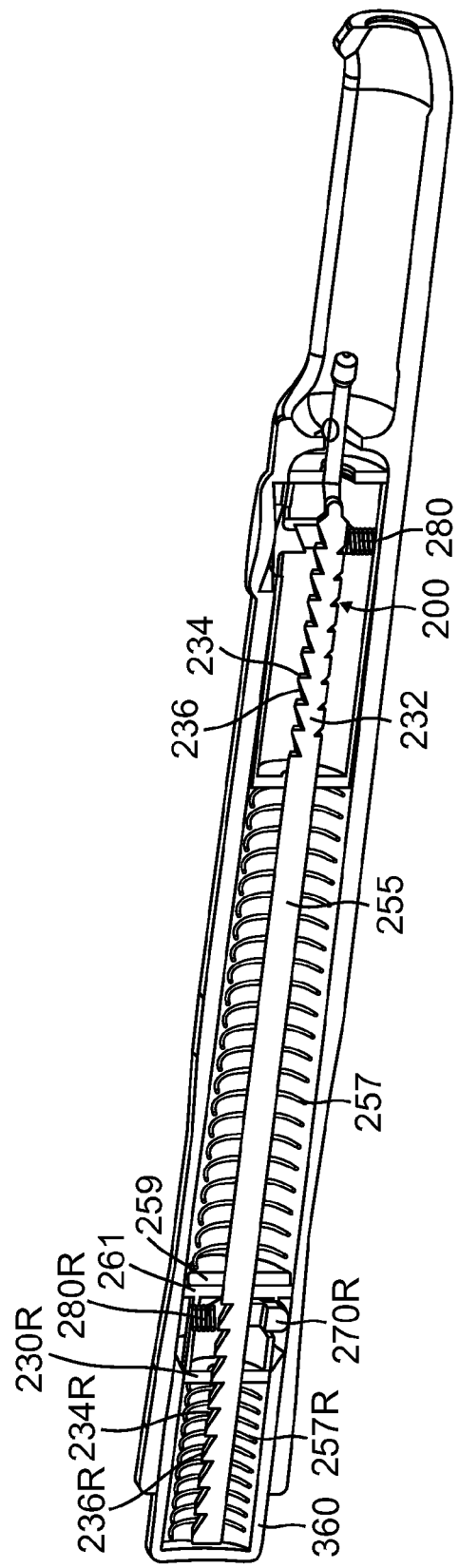
FIG. 8 is a cross-sectional view taken down the middle of the pen of the present invention to better illustrate a portion of the operating mechanism illustrated in FIG. 5.

Referring to FIG. 5 and a portion of FIGS. 7 and 8, there is illustrated the operating mechanism 230 for the dual chamber cartridge 10. The mechanism includes a pair of pistons 210 and 220 which are respectively used to engage a respective pocket 72 and 74 of the two-pocket plunger 54 used with the dual chamber cartridge and a ratchet mechanism 230 which is engaged by a tooth member 270 as will be discussed to move the two pistons 210 and 220 in the forward direction to push the plunger 54 forwardly to dispense selected compounds such as tooth whitening compounds 100 and 110 (or dental bonding or filling compound or adhesive compound or other selected compounds as defined above) from the cartridge 10 within the pen 300. The mechanism 230 also contains a moving ratchet tooth member and housing 270 to engage each ratchet tooth 232 having a vertical wall 234 and a rearwardly slanted top surface 236 by a given amount and the ratchet tooth slides down the slanted top surface 236 until it is adjacent the vertical wall 234 of the next ratchet tooth 232 to move the pistons 210 and 220 forward. The pen 300 has an interior chamber 310 which receives the ratchet mechanism 230 which also has a pulling or reset bar at its end 16 which extends out an opening 330 in the rear end 16 of the pen 300 so that the entire operating mechanism 230 can be pulled backward in the interior chamber 310 of the tooth whitening pen 300 for the insertion of a fresh cartridge 10 after a specific cartridge has been used up.

Figure 6:
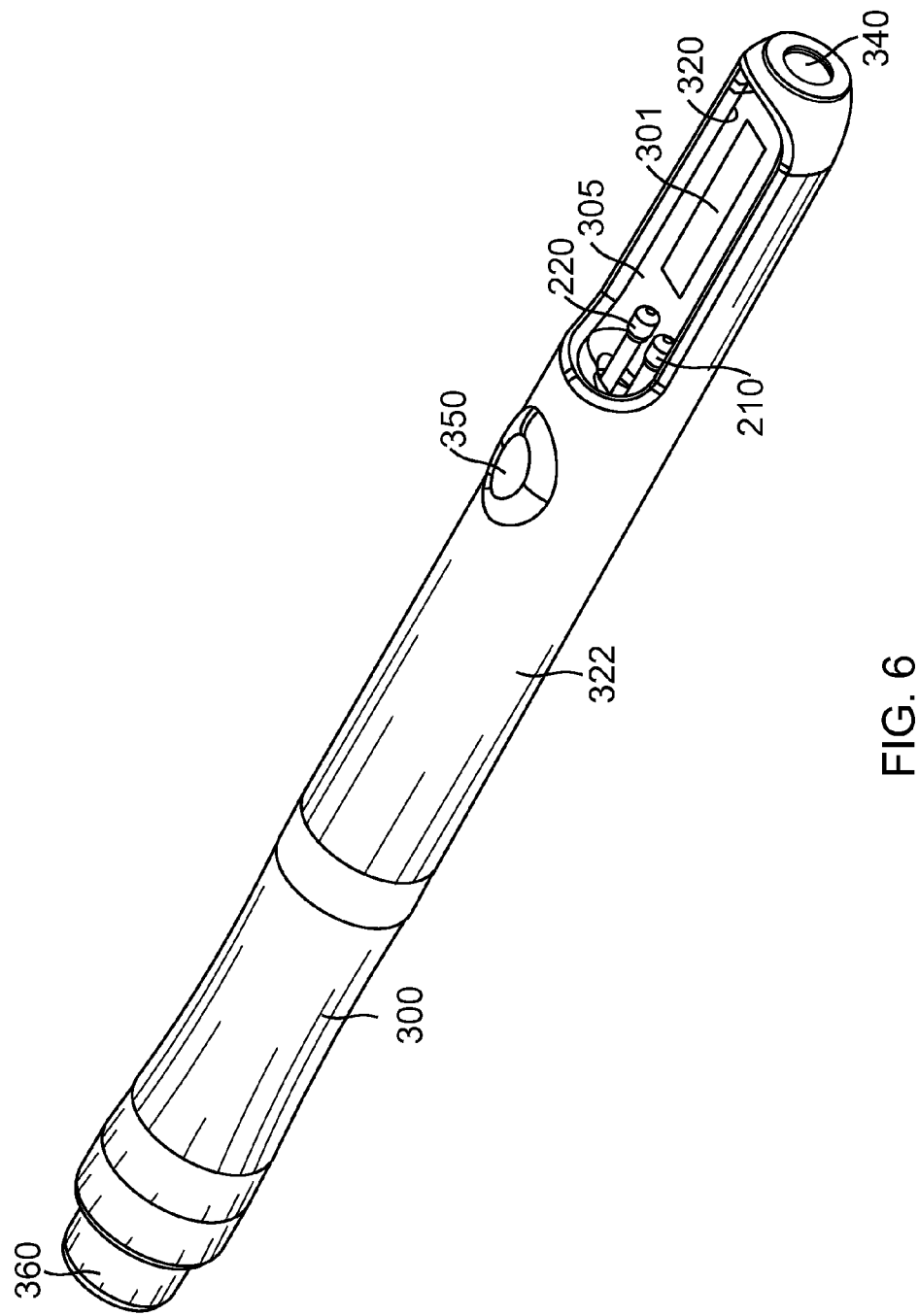
FIG. 6 is a top perspective view of the pen of the present invention with the entire operating mechanism illustrated in FIG. 5 inserted into an interior chamber of the pen.

Referring to FIG. 6, there is illustrated a top perspective view of the present invention pen 300 which is used to retain the removable cartridge 10. The pen 10 has an interior chamber 310 which contains the operating mechanism 230 illustrated in FIG. 5 where the two pistons 210 and 220 are shown in the condition where they are about to dispense compounds from a cartridge to be inserted in the pen. The pen 300 further includes and interior cylindrical sidewall 320 and an exterior cylindrical wall 322 and an open front 340 through which the front tip 22 of the cartridge 10 extends, There is also a back pushing member 350 which is used to push the cartridge forward along with the mechanism 230 to push the pistons 210 and 220 forward to enable the pistons 210 and 220 to move against the back of the plunger 54 and dispense the selected compound. Also illustrated is a back resetting member 360 which will be described later.

Referring to FIGS. 7 and 8, there is illustrated the operating mechanism 200 within the pen. The mechanism involves a pushed down tooth operator 260 which is pushed down by the back pushing member 350 and a tooth operating mechanism 265 which pushes down on moving ratchet tooth 270 which engages each of the ratchet teeth 232 as previously described. The moving ratchet tooth engaging member 270 also has a spring mechanism 280 which causes the moving ratchet tooth engaging member 270 to move upwardly after it engages a ratchet tooth 232 and moves it forward and is adjacent a vertical wall 234 so it is moved upwardly to come in contact with the next slanted top wall 236 of a ratchet tooth 232. As illustrated in FIGS. 7 and 8, when a downward force from the back pushing member 350 is exerted on and pushed down on the tooth operator 260 which in turn exerts a downward force on the moving ratchet tooth engaging member 270, the member 270 engages a downward sloped wall 236 of a ratchet tooth 232 and slides downwardly against the ratchet to move the ratchet forward by the given distance of the downward sloped wall 236 until it arrives at the vertical wall 234 of the next ratchet tooth 232 and the spring mechanism 280 causes the moving ratchet tooth engaging member 270 to be pushed upwardly to come in contact with the next top sloped wall 236 of the next ratchet tooth 232 so that a downward force from the pushed down tooth operator 260 causes the ratchet tooth to slide downwardly against the next sloped top 236 or the next ratchet tooth 232 and therefore move the ratchet forward, thereby moving the pistons 210 and 220 forward.

Referring to FIGS. 5, 7 and 8, the ratchet tooth assembly 230 including ratchet teeth 232 is affixed to and is part of a longitudinal bar 255 surrounded by a compression spring 257 affixed to a plate 259 which is attached to a rear ratch tooth housing 261 which includes rear ratchet teeth 232R having a rear vertical wall 234R and a rear slanted wall 236R for each ratchet tooth 232R with an inverted rear ratchet tooth engaging member 270R with an upside down spring mechanism 280R. As the first ratchet mechanism 230 is moved forwardly as previously described, the bar 255 moves forwardly causing plate 259 to which the bar 255 is attached to move forwardly which in turn causes the compression housing plate 259 to move forwardly which in turn causes the rear ratchet tooth housing 261 to move forwardly causing the rear ratchet tooth engaging member to move downwardly against and to engage a rear slanted top wall 236R of a rear ratchet tooth 232R until it comes in contact with a rear ratchet tooth vertical wall 234R. The upside down spring 280R causes the moving ratchet tooth engaging member 270R to move upwardly after it engages a ratchet tooth 232R and moves it forward and is adjacent a vertical wall 234R so it is moved upwardly to come in contact with the next rear slanted top wall 236R of a rear ratchet tooth 232R. During this process, main compression spring 257 and a rear ratchet tooth compression spring 257R surrounding rear ratchet tooth assembly 230R are compressed.

After the cartridge 10 is used up, the back resetting member 360 is pulled away from the back wall 16, overcoming the compression force of compression springs 257R and 257 to reset the entire ratchet tooth assemblies 230 and 230R so the pistons 210 and 220 are moved away from the front opening 340 to leave the opening 305 into which a new cartridge can be inserted.

Figure 9:
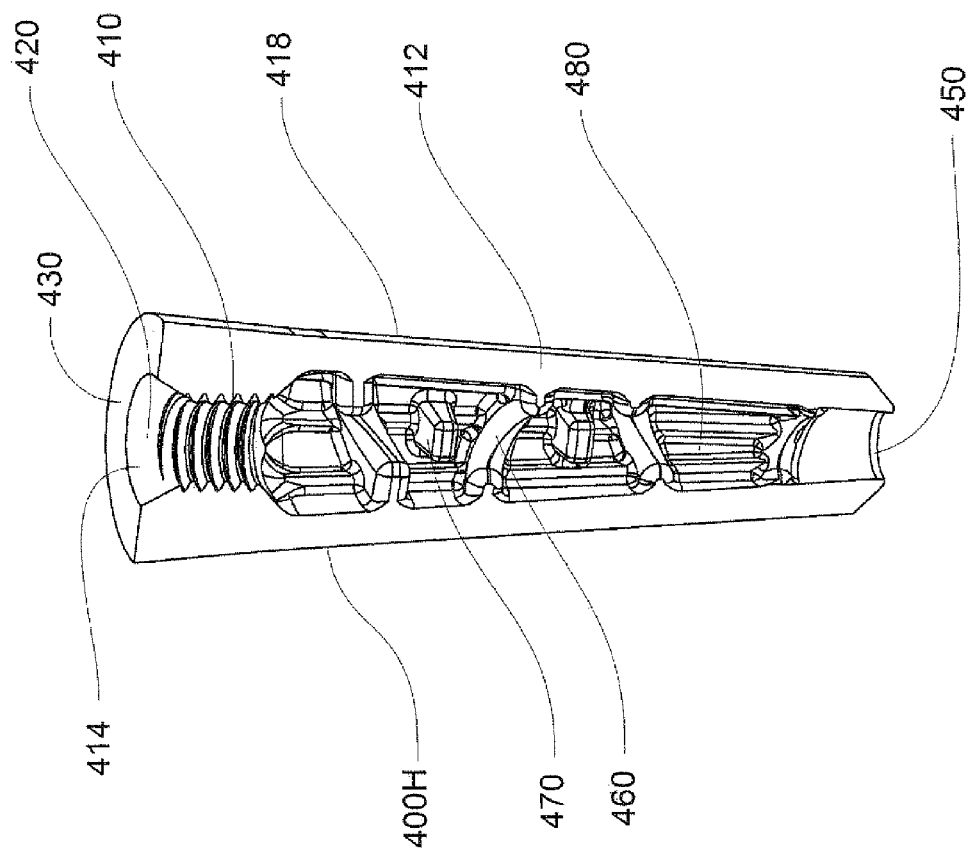
FIG. 9 is a longitudinal cross-sectional view of the mixing nozzle of the present invention used with a cartridge having a divided interior housing two separate compounds.
Figure 9A:
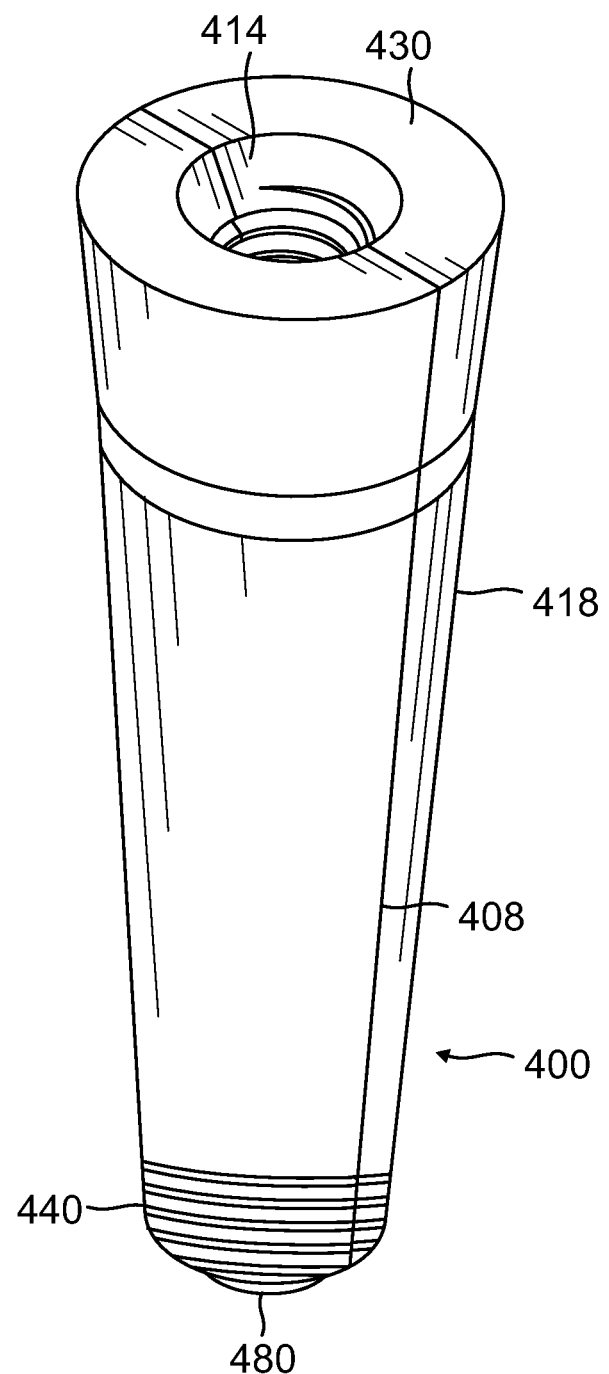
FIG. 9A is perspective view of the entire mixing nozzle including the two halves as illustrated in FIG. 9 sonic welded together at their respective mating surfaces at a location illustrated along a seam line to form an entire mixing tip.
Figure 14:
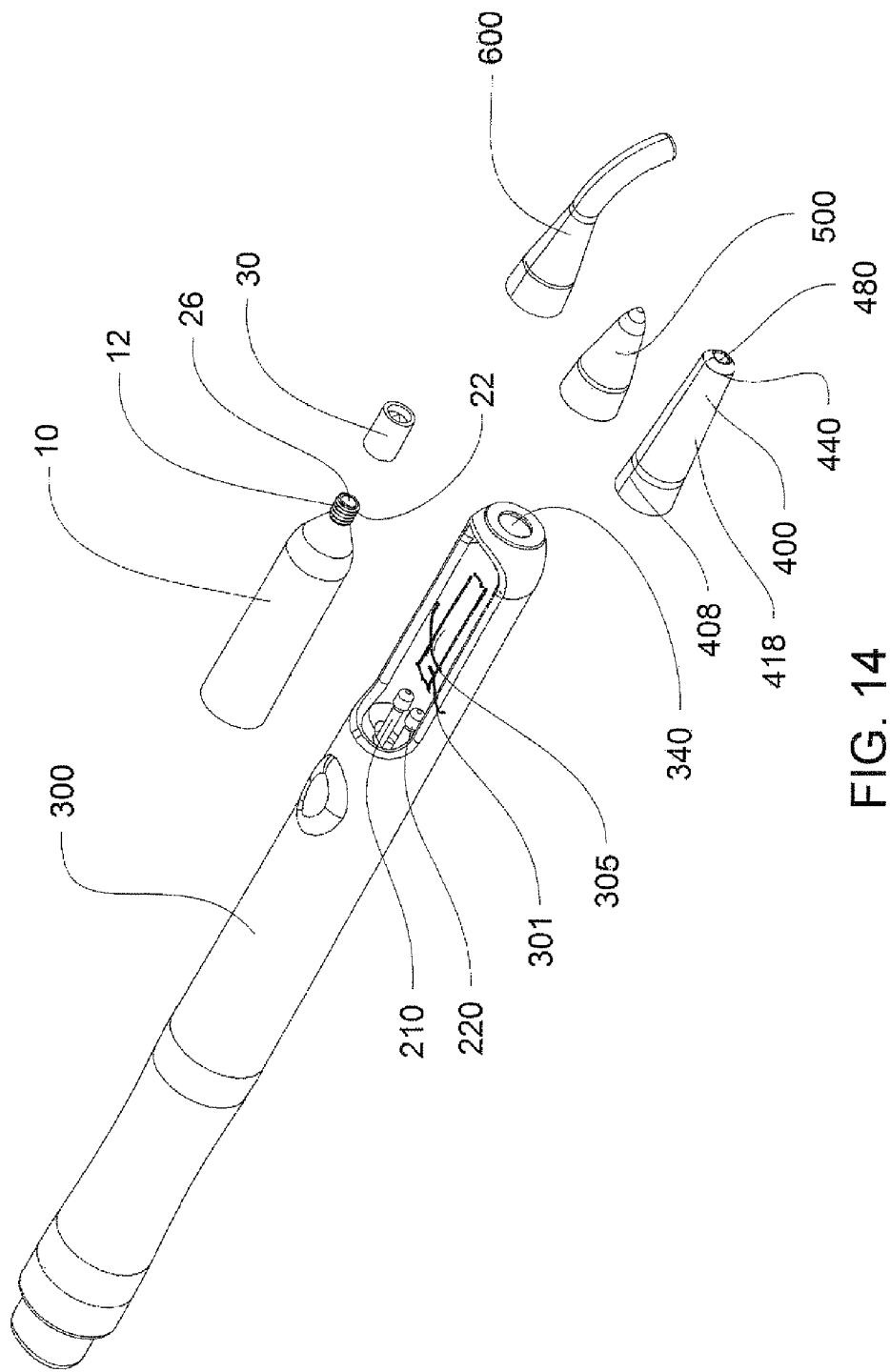
FIG. 14 is an exploded view illustrating the pen with the dual piston operating mechanism illustrated in FIG. 7 inserted into the pen, a dual chamber cartridge before it is inserted into the pen, the mixing nozzle, the straight nozzle and the bent horn nozzle.

Referring to FIGS. 9, 9A and 14, there is illustrated a cross-sectional view of one half 400H of the mixing nozzle 400 which is used with a dual chamber cartridge. The mixing nozzle 400 has internal threads 410 on its internal surface 420 adjacent its rear end 430 and on its external surface 418 external threads 440 adjacent its front end 450 and contains a multiplicity of semi-closed shelves 460 and also straight shelves 470 so that as the compounds 100 and 110 are driven through the mixing nozzle 400, the angular shelves 460 and the straight shelves 470 cause the compounds 100 and 110 to mix together and go through a series of angular shelves 460 and straight shelves 470 to make sure that the compound is fully mixed when it gets to the opening 480 of the mixing chamber 400. A rear opening 414 permits the compounds 100 and 110 to enter the mixing tip 400 after it is screwed onto the threads 24 of tip 26 of capsule 10. FIG. 9 illustrates one half of the mixing nozzle. The opposite half is a mirror image of half 400H. The two halves of sonic welded together along their longitudinal interior faces 412 to form a complete mixing nozzle 400 illustrated in FIGS. 9A and 14. Referring to FIG. 14, a seam line 408 illustrates the location of the sonic weld.

A key innovation of the present invention mixing nozzle 400 is that it is comprised of internal built in shelves which thoroughly mix the compound portions as they are forced through the mixing nozzle. This is a major improvement over the prior art where an insert is placed into a chamber and compounds mixed through the insert which leads to less mixing and much more inefficiency in the mixing.

Figure 10:
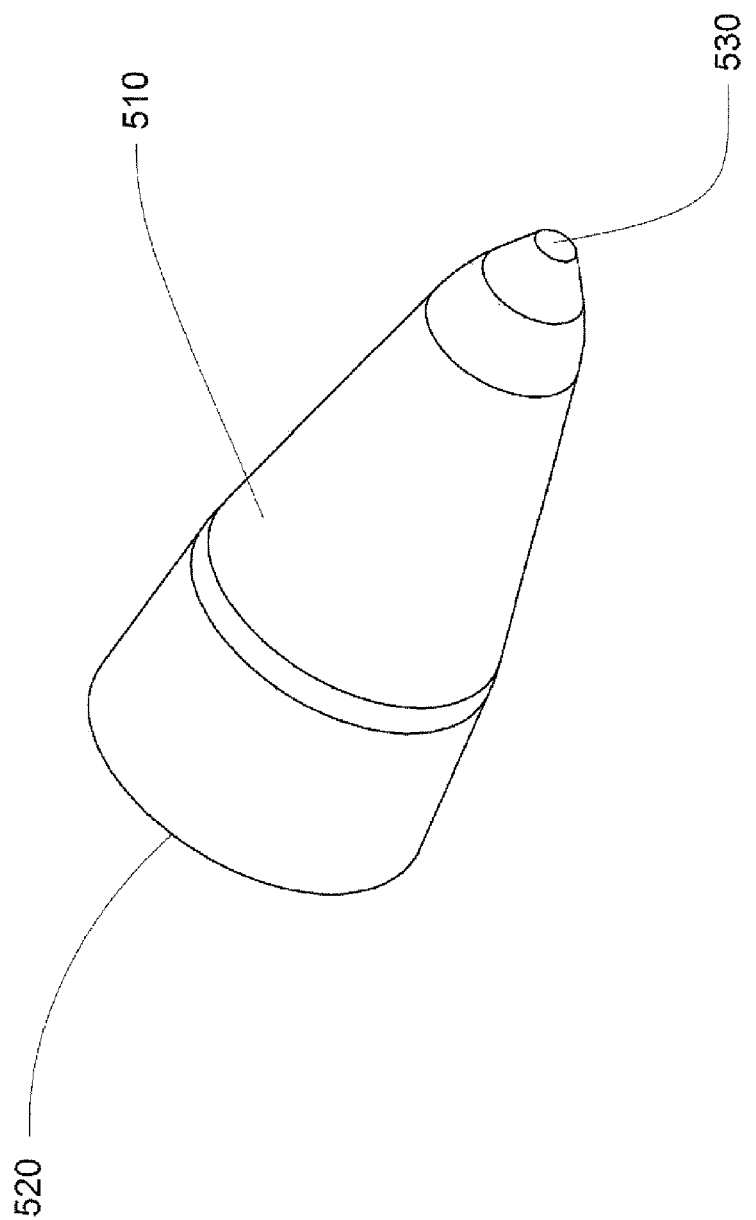
FIG. 10 is a perspective view of a straight dispensing nozzle used with a single chamber cartridge or used with a mixing tip and a dual chamber cartridge.
Figure 11:
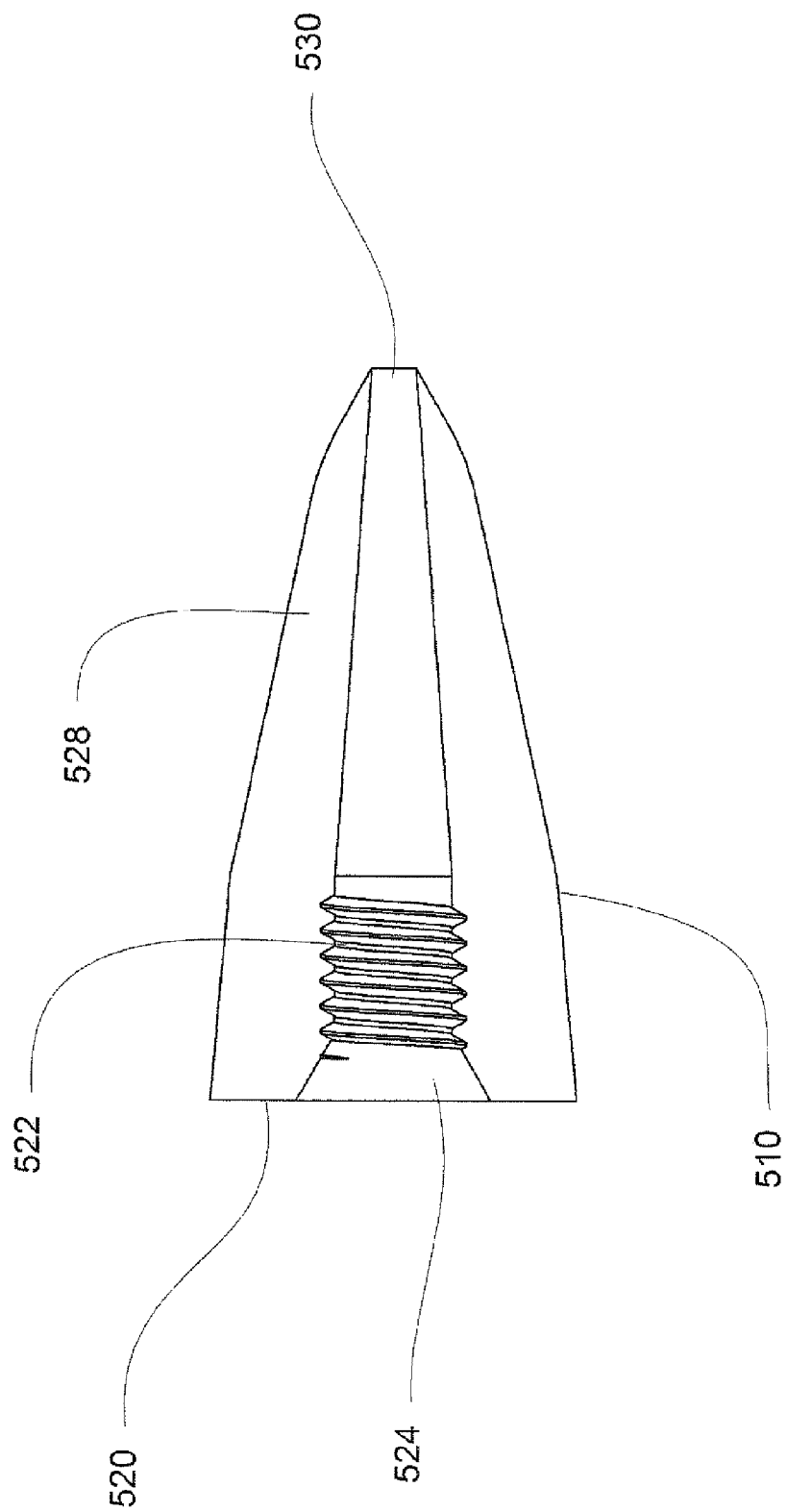
FIG. 11 is a cross-sectional view of the straight dispensing nozzle illustrated in FIG. 10.

Referring to FIGS. 10 11 and 14, there is illustrated a straight applicator 500 which contains an exterior surface 510 and an interior chamber 528 which has a widened end 520 with interior threads 522 surrounding a rear opening 524 that either thread around the end of the mixing tip or thread around the threaded end of the compound capsule and a front opening 530 through which the compound is dispensed. The compound enters through rear opening 524 and exits through front opening 530.

Figure 12:
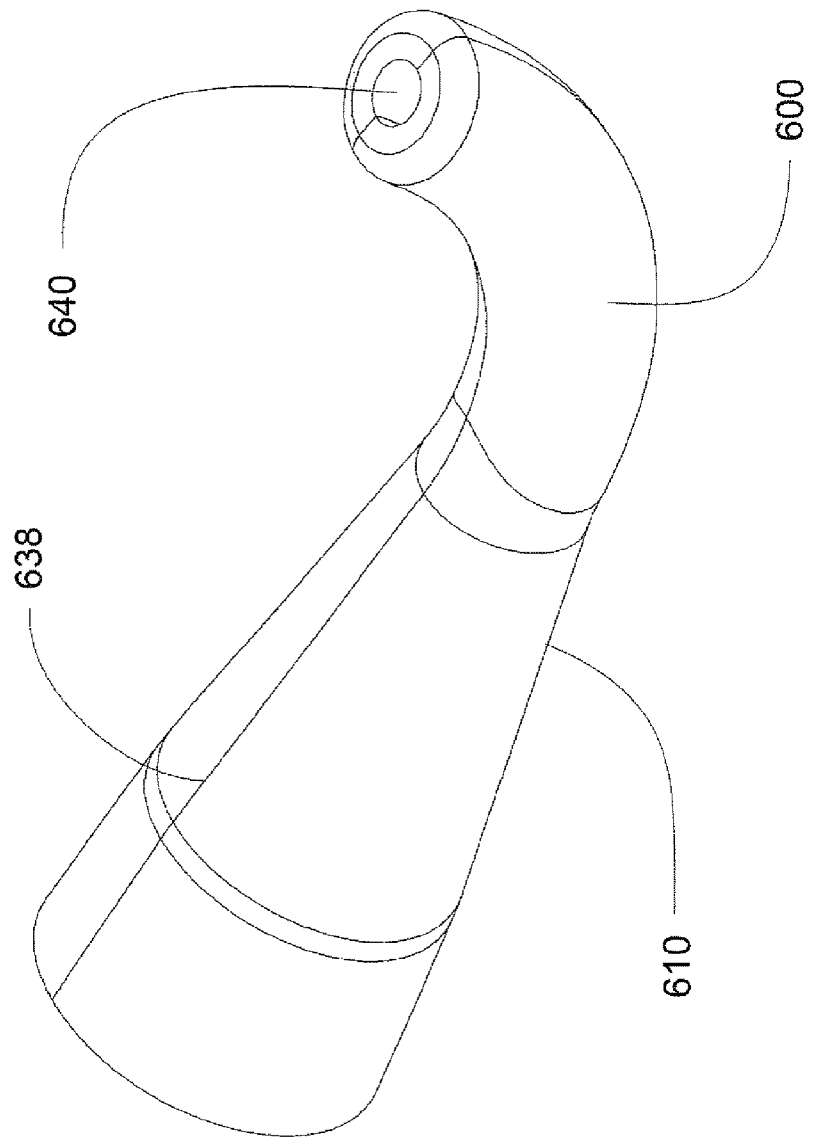
FIG. 12 is a perspective view of a bent horn tip dispensing nozzle used with a single chamber cartridge or used with a mixing tip dual chamber cartridge.
Figure 13:
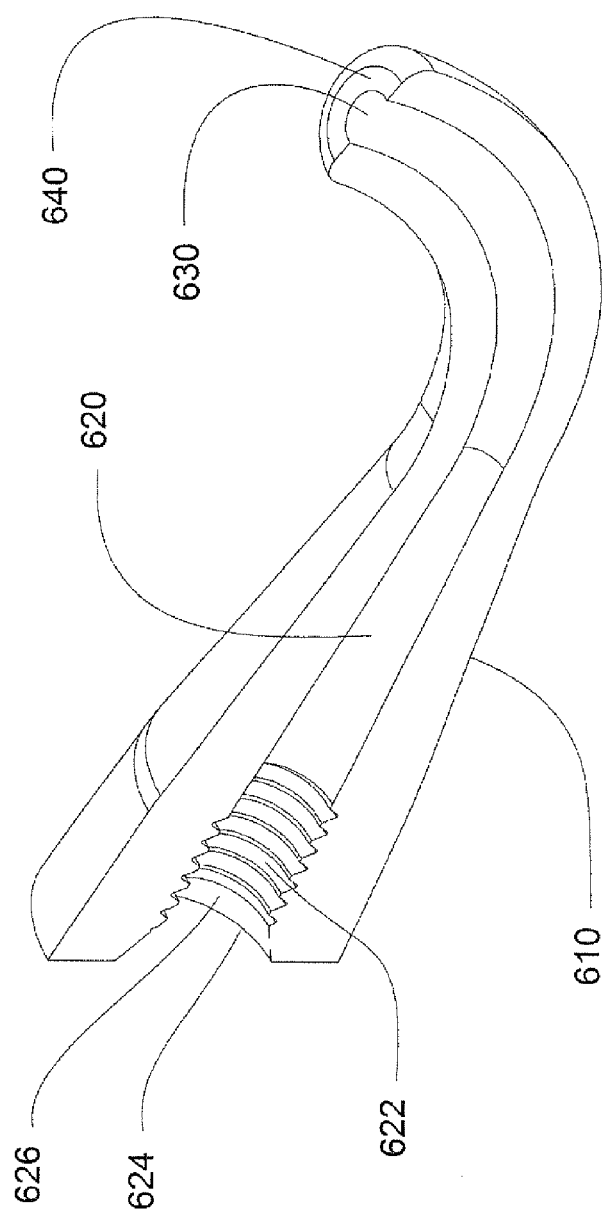
FIG. 13 is a cross-sectional view of the bent horn tip dispensing nozzle illustrated in FIG. 12.

In an alternative embodiment illustrated in FIGS. 12, 13 and 14, the applicator is a horn-shaped applicator 600 which has an exterior wall 610 and an interior chamber 620 which has a rear opening 624 and a rear interior wall 620 having threads 622 which can be threaded onto the end of the mixing tip or threaded onto the end of the tooth whitening compound cartridge and also has an opening 630 in front end 640 which is bent at an angle so that the tooth whitening compound can be applied to rear surface or to teeth near the back of the patient's mouth, the dental bonding compound can be applied to rear teeth fillings and the adhesive compound can be applied at a rear area of objects to be bonded together. The selected compounds enter from rear opening 624 and exits through front opening 640.

Figure 15:
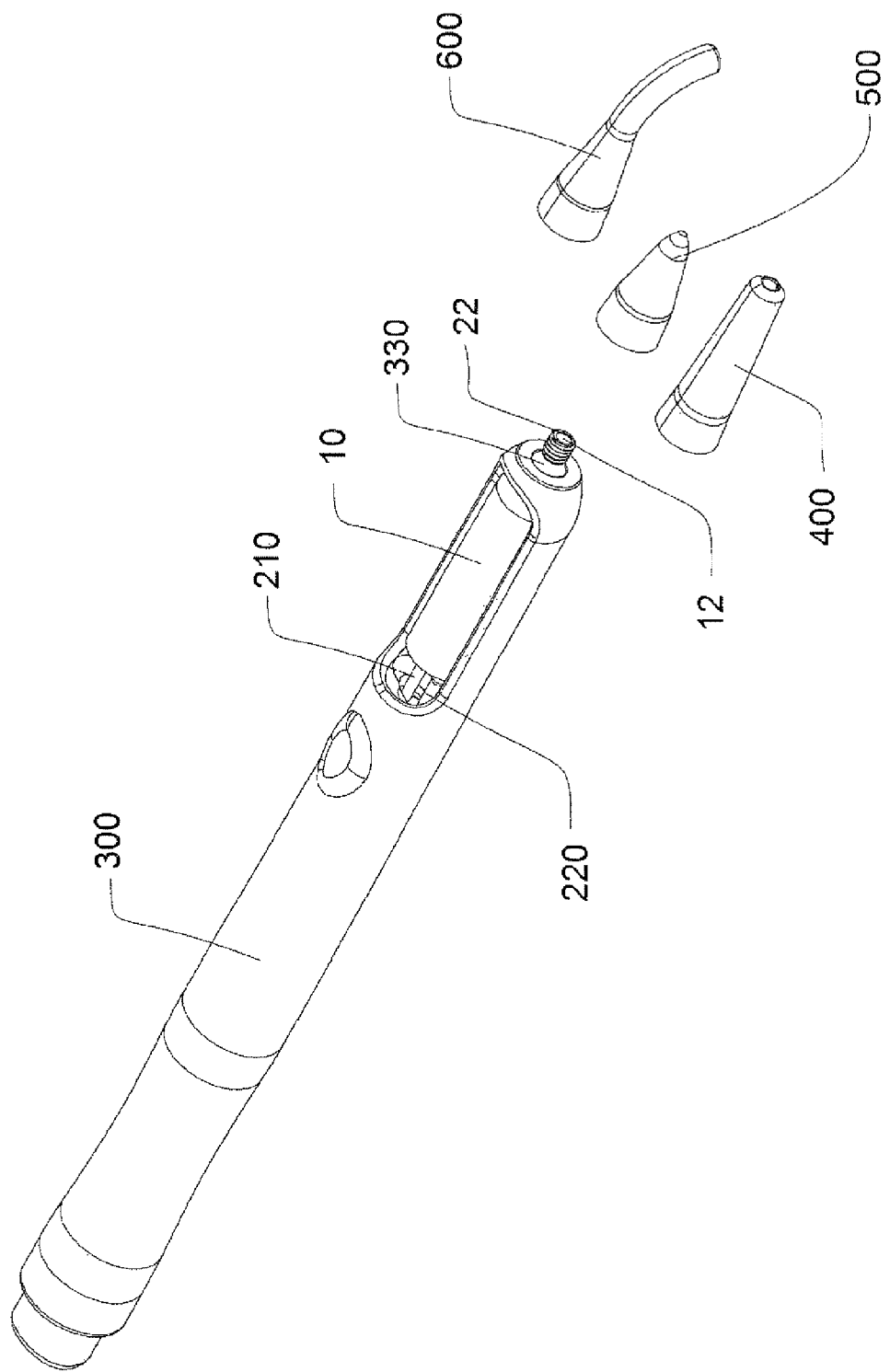
FIG. 15 is an exploded view illustrating the pen with the dual piston operating mechanism illustrated in FIG. 7 inserted into the pen, a dual chamber cartridge after it is inserted into the pen, the mixing nozzle, the straight nozzle and the bent horn nozzle.

Referring to FIG. 14 (before the cartridge 10 is inserted into the pen 300) and FIG. 15 (after the cartridge 10 is inserted into the pen 300) there is illustrated an exploded view showing how the mixing pen operates. The cartridge 10 containing the compound 100 and 110 is inserted into an opening 305 near the front of the applicator pen 300 and into interior chamber 305 where the pockets 72 and 74 of the plunger 54 are retained against the dual pistons 210 and 220 and the front tip 12 of the cartridge 10 extends out of the opening 340 in the pen 300. The anti-rotation slit 44 on the cartridge is placed into the anti-rotation longitudinal stop shelf 301 in chamber 305 so the cartridge 10 will not rotate once inside the pen. The sealing cap 30 is shown removed from the cartridge 10. After the cartridge is inserted into the pen, the cap 30 is used to penetrate the frangible seal 26 of the tip 22 of the cartridge 10 which extends out of the opening 340 in the pen 300 and thereafter either the mixing tip 400 is threaded onto the cartridge 10 if it is a dual chamber cartridge and either the straight applicator 500 or the horn-shaped applicator 600 is threaded onto the mixing tip 400 so that as the ratchet mechanism 230 causes the pistons 210 and 220 to move toward the front of the pen 300, the pistons 210 and 220 push on the back of the plunger 50 causing the plunger 50 to move each compound 100 and 110 from each separate section of the cartridge 10 into the mixing tip 400 where the compounds 100 and 110 are mixed and then exit the mixing tip 400 into the applicator so that the mixed tooth whitening compound is either placed in a dental tray or placed on the patient's tooth.

Figure 16:
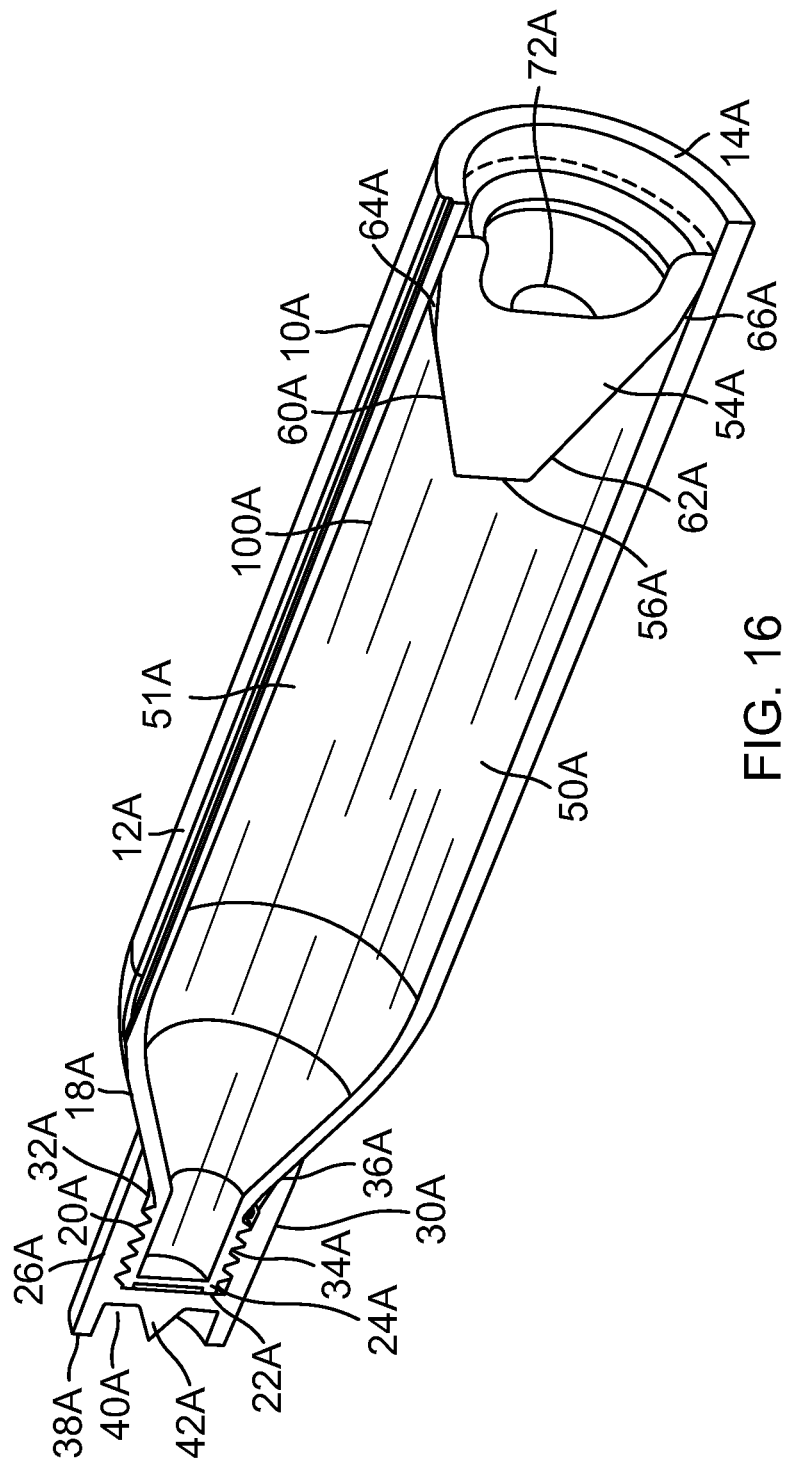
FIG. 16 is a side cross-sectional view of a second embodiment of the unidose single use cartridge illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston.

Referring to FIG. 16, there is illustrated a side cross-sectional view of a second embodiment of the unidose single use cartridge with sealing cap affixed, illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston.

The exterior of the cartridge for the second embodiment looks the same as FIGS. 1, 2 and 3. The cartridge 10A has a single interior chamber 50A with a single compound 100A retained in the interior chamber 50A. A rear plunger 54A having an interior face 56A is used to push the compound 100A in the interior chamber 50A forward and out of the cartridge 10A. The rear plunger 54A has a pair of opposed rear angular sides 60A and 62A extending from opposite ends of the interior face 56A and respectively ending in rear sidewalls 64A and 66A forming a seal against the interior sidewall 51A of the cartridge 10A, each rear end 64A and 66A of the plunger 54A forming the sidewalls of a pocket 72A to receive the pushing piston from the retaining pen.

The remaining rear and front of the cartridge 10A has the same parts as illustrated in FIGS. 1, 2,3 and 4 with the corresponding part numbered the same with an "A" after each corresponding part number. The corresponding parts 14A, 18A 20A, 22A, 24A, 26A, 30A, 32A, 34A, 38A, 40A and 42A function and operate the same as previously described and will be repeated. The length and width can be the same as for the double chamber cartridge or for the single cartridge, it can be shorter in length and diameter which would require a smaller pen. In the interests of efficiency, it is anticipated that the single chamber cartridge 10A will have the same length "L1" and the same varying diameter as the dual chamber cartridge.

Figure 17:
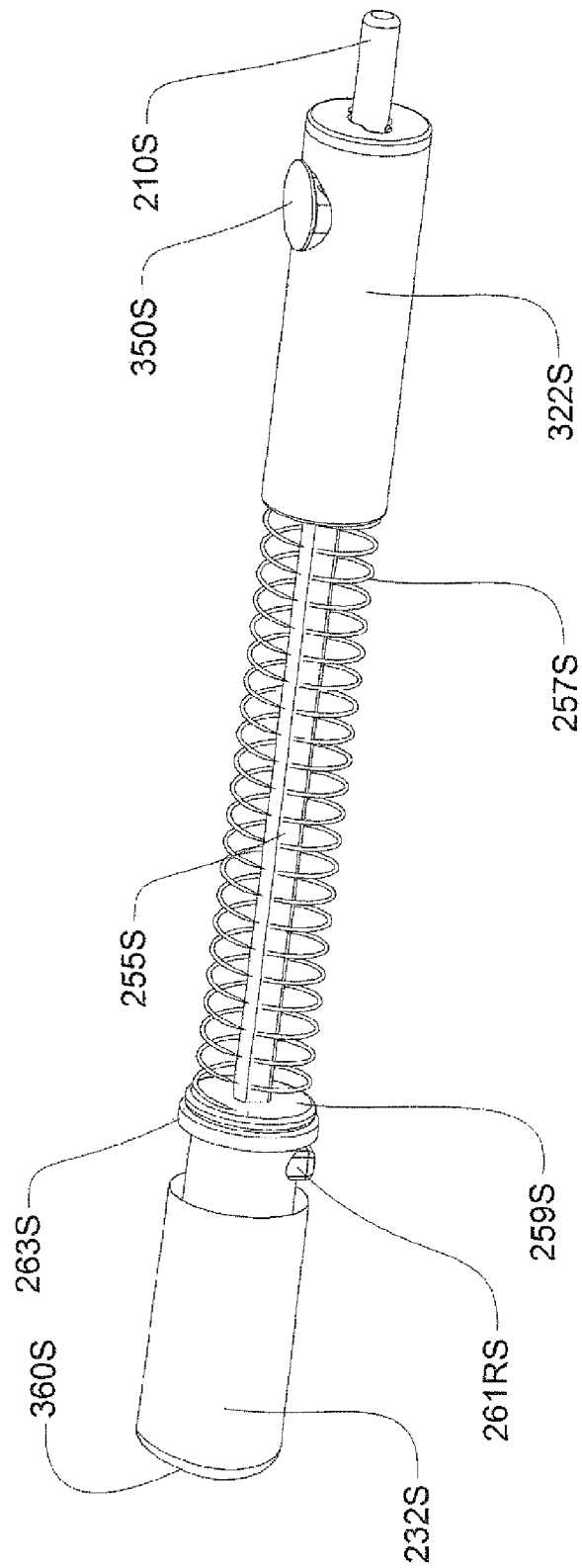
FIG. 17 is a perspective view of the entire operating mechanism for the interior single chamber cartridge illustrated in FIG. 16.
Figure 18:
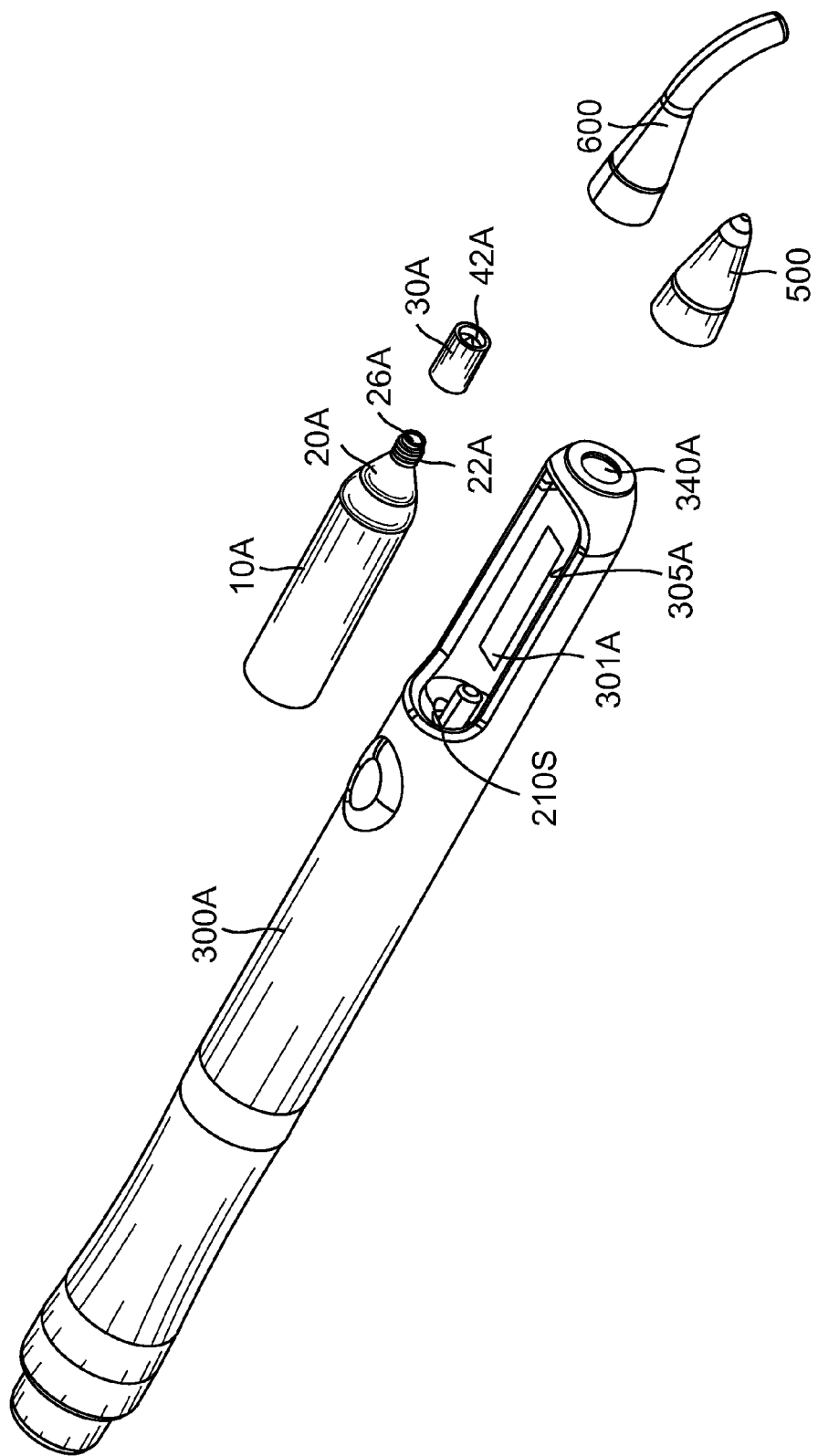
FIG. 18 is an exploded view illustrating the pen with the single piston operating mechanism illustrated in FIG. 17 inserted into the pen, a single chamber cartridge before it is inserted into the pen, the mixing nozzle, the straight nozzle and the bent horn nozzle.
Figure 19:
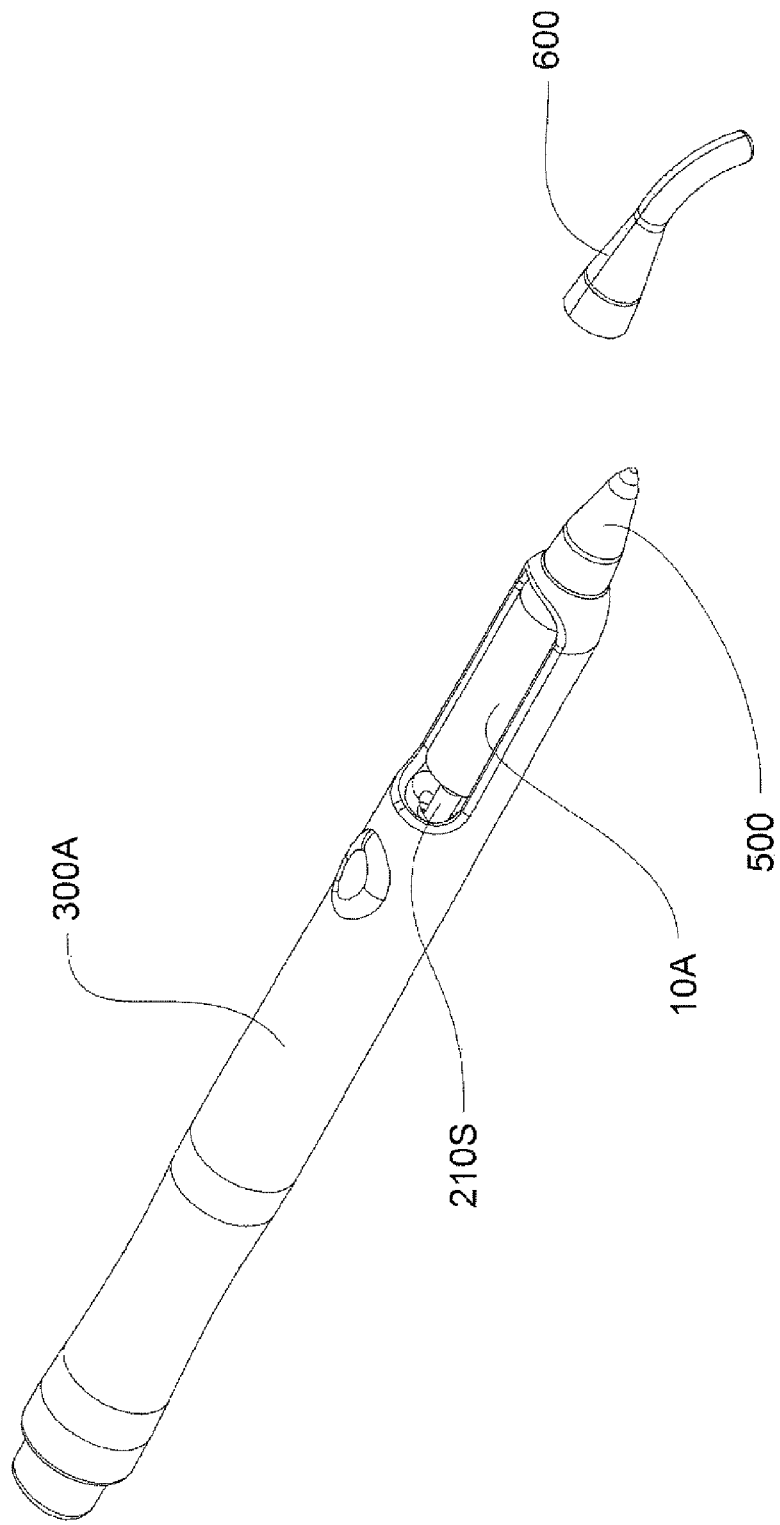
FIG. 19 is an exploded view illustrating the pen with the single piston operating mechanism illustrated in FIG. 17 inserted into the pen, a single chamber cartridge after it is inserted into the pen, the mixing nozzle, the straight nozzle and the bent horn nozzle.

The operating mechanism for the single chamber cartridge 10A is the same as the operating mechanism for the dual chamber cartridge 10 illustrated in FIGS. 5, 6, 7 and 8 with the same parts except that the operating mechanism for a single chamber cartridge has only one piston 210S (see FIG. 17) extending from the ratchet tooth assembly. Therefore, the operation as described for the illustrations in FIGS. 5, 6, 7 and 8 will not be repeated. The corresponding parts visible in FIGS. 17, 18 and 19 are the same as in FIGS. 5, 6, 7 and 8 with an "S" at the end of each number.

The operation of the pen 300A with a single chamber cartridge 10A is the same as illustrated in FIGS. 14 and 15 with the corresponding parts having the same number with an "A" added to the number. However, since there is only one compound, a mixing nozzle is not necessary. Therefore, after the single chamber cartridge 10A is inserted into the pen 300A and the frangible seal 26A is penetrated by the tooth 42A, either a straight nozzle 500 or a bent horn shaped nozzle 600 is threaded onto the threads 22A of the single chamber cartridge 10A. As compound 100A is pushed through the internal chamber 50A by plunger 54A pushed by the ratchet mechanism advancing single piston 210S, the compound 100A exits the cartridge 10A and enters a nozzle through which the compound 100A is dispensed.

Except for combining two compounds in a mixing nozzle, the operation after the compound is pushed out of the cartridge is the same.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An apparatus for removably retaining a single use cartridge and dispensing compounds from the single use cartridge, comprising:

a. a single use cartridge having an exterior surface which surrounds an interior circumferential wall surrounding interior dual chambers separated by an interior longitudinal dividing wall and a rear opening leading to the interior dual chambers, two compounds with a respective compound retained within a respective one chamber of the dual interior chambers and separated by the interior longitudinal dividing wall, a plunger having front interior surfaces aligned with a respective one chamber and having sidewalls which serve as a seal against the interior circumferential wall to prevent the compounds from flowing out of the rear opening, the plunger having a pair of rear spaced apart pockets respectively aligned with a respective one of the dual chambers, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the dual interior chambers, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the single use cartridge;

b. an operating mechanism for the dual chamber cartridge, the operating mechanism placed in a dispensing apparatus and the operating mechanism including a pair of pistons which are respectively used to engage a respective rear pocket of the plunger used with the dual chamber cartridge and a ratchet mechanism which is engaged by a tooth member to move the two pistons in a forward direction to push the plunger forwardly to dispense the compounds from the cartridge when the cartridge is placed in the dispensing apparatus at a location in front of the dual pistons, the operating mechanism includes a moving ratchet tooth member and housing to engage each ratchet tooth having a vertical wall and a rearwardly slanted top surface by a given amount and the ratchet tooth slides down the slanted top surface until it is adjacent a vertical wall of a next ratchet tooth in a ratchet tooth assembly to move the pistons forward; and c. the dispensing apparatus includes an exterior surface with a rear opening and a front tip dispensing opening and surrounding an interior chamber which receives the operating mechanism which also has a resetting bar at its end which extends out the opening in the rear end of the dispensing apparatus so that the entire operating mechanism is pulled backward in the interior chamber of the dispensing apparatus for the insertion of a fresh cartridge after a specific cartridge has been used up, the dispensing apparatus includes the interior chamber which contains the operating mechanism where the two pistons are adjacent an interior opening where the single use cartridge is inserted in the dispensing apparatus, the dispensing apparatus includes an interior cylindrical sidewall and an exterior cylindrical wall and an open front through which the front tip of the cartridge extends, and a back pushing member which is used to push the cartridge forward along with the mechanism to push the pistons forward to enable the pistons to move into the pockets against the back of the plunger and dispense the compounds through the opening in the nozzle tip of the cartridge.

2. The apparatus in accordance with claim 1, further comprising: the operating mechanism further includes a pushed down tooth operator which is pushed down by the back pushing member and a tooth operating mechanism which pushes down on moving ratchet tooth which sequentially engages each ratchet tooth, the moving ratchet tooth engaging member also has a spring mechanism which causes the moving ratchet tooth engaging member to move upwardly after it engages a ratchet tooth and moves it forward and is adjacent a vertical wall so it is moved upwardly to come in contact with the next slanted top wall of a ratchet tooth, and when a downward force from the back pushing member is exerted on and pushed down on the tooth operator which in turn exerts a downward force on the moving ratchet tooth engaging member, the member engages a downward sloped wall of a ratchet tooth and slides downwardly against the ratchet tooth to move the ratchet forward by the given distance of the downward sloped wall until it arrives at the vertical wall of the next ratchet tooth and the spring mechanism causes the moving ratchet tooth engaging member to be pushed upwardly to come in contact with the next top sloped wall of the next ratchet tooth so that a downward force from the pushed down tooth operator causes the ratchet tooth to slide downwardly against the next sloped top of the next ratchet tooth and therefore move the ratchet forward, thereby moving the pistons forward.

3. The apparatus in accordance with claim 2, further comprising:

a. the ratchet tooth assembly includes ratchet teeth affixed to and part of a longitudinal bar surrounded by a compression spring affixed to a plate which is attached to a rear ratchet tooth housing which includes rear ratchet teeth having a rear vertical wall and a rear slanted wall for each ratchet tooth with an inverted rear ratchet tooth engaging member with an upside down spring mechanism so that as the first ratchet mechanism is moved forwardly the bar moves forwardly causing a plate to which the bar is attached to move forwardly which in turn causes a compression housing plate to move forwardly which in turn causes the rear ratchet tooth engaging member to move forwardly and downwardly against and to engage a rear slanted top wall of a rear ratchet tooth until it comes in contact with a rear ratchet tooth vertical wall, the upside down spring causes the moving ratchet tooth engaging member to move upwardly after it engages a ratchet tooth and moves it forward and is adjacent a vertical wall so it is moved upwardly to come in contact with the next rear slanted top wall of a rear ratchet tooth; and b. a main compression spring surrounds the bar and a rear ratchet tooth compression spring surrounding the rear ratchet tooth assembly are compressed and after the cartridge is used up, the back resetting member is pulled away from the back wall, overcoming the compression force of the main compression spring and rear ratchet tooth compression spring to reset the entire ratchet tooth assemblies so the pistons are moved away from the front opening to leave the opening into which a new cartridge is inserted.

4. The apparatus in accordance with claim 1, further comprising:
   a. the exterior wall of the single use cartridge includes an anti-rotation slit; and
   b. the opening in the dispensing apparatus into which the single use cartridge is inserted includes an anti-rotation shaft inserted into the anti rotation slit.

5. The apparatus in accordance with claim 1, further comprising: the interconnecting section is frustum shaped with a widened end adjacent a body of the single use cartridge and a narrow end adjacent the nozzle tip of the single use cartridge.

6. The apparatus in accordance with claim 1, further comprising:
   a. a mixing nozzle having internal threads on an internal surface adjacent a rear open rear end of the mixing nozzle by which the mixing nozzle is threaded onto the threads of the nozzle tip of the cartridge, and external threads on a front surface adjacent a front end of the mixing nozzle, an interior of the mixing nozzle including a multiplicity of angular shelves and straight shelves formed into the interior of the mixing nozzle in longitudinally arranged sets so that as the compounds are driven through the mixing nozzle, the angular shelves and the straight shelves cause the compounds to mix together and go through a series of angular shelves and straight shelves to make sure that the compounds are fully mixed when the compounds are pushed to a front opening in the mixing nozzle.

7. The apparatus in accordance with claim 6, further comprising: the mixing nozzle is comprised of two mirror image longitudinal halves which are sonic welded together.

8. The apparatus in accordance with claim 6, further comprising:
   a. a straight applicator which includes an exterior surface and an interior chamber which has a widened end with interior threads surrounding a rear opening by which the straight applicator is threaded onto the exterior threads of the mixing nozzle so that compounds are pushed out of the cartridge into the mixing nozzle and then mixed compounds are pushed out of the mixing nozzle into the straight applicator and then pushed out a front opening in the straight applicator.

9. The apparatus in accordance with claim 6, further comprising:
   a. a horn-shaped applicator which has an exterior wall and an interior chamber which has a rear opening and a rear interior wall having threads adjacent the rear opening by which the horn shaped nozzle is threaded onto the exterior threads of the mixing nozzle so that compounds are pushed out of the nozzle tip of the cartridge and into the mixing nozzle, the mixed compounds are then pushed out of the mixing nozzle and into the horn shaped applicator and then pushed out of an opening in the horn shaped applicator.

10. The apparatus in accordance with claim 1, further comprising: the compounds are selected from the group consisting of tooth whitening compounds, dental bonding and filling compounds, adhesive compounds, jells, creams, and finely ground powders.

11. The apparatus in accordance with claim 1 further comprising: the dual chambers are the same size.

12. The apparatus in accordance with claim 1 further comprising: the dual chambers are of different sizes.

13. An apparatus for removably retaining a single use cartridge and dispensing a compound from the single use cartridge, comprising:
   a. a single use cartridge having an exterior surface which surrounds an interior circumferential wall surrounding an interior chamber and a rear opening leading to the interior chamber, a compound retained within the interior chamber, a plunger having a front interior surface aligned with the interior chamber and having sidewalls which serve as a seal against the interior circumferential wall to prevent the compound from flowing out of the rear opening, the plunger having a rear pocket, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the interior chamber, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the cartridge;
   b. an operating mechanism for the single chamber cartridge, the operating mechanism placed in a dispensing apparatus and the operating mechanism including a piston which is used to engage the rear pocket of the plunger and a ratchet mechanism which is engaged by a tooth member to move the piston in a forward direction to push the plunger forwardly to dispense the compound from the single use cartridge when the single use cartridge is placed in the dispensing apparatus at a location in front of the piston, the operating mechanism includes a moving ratchet tooth member and housing to engage each ratchet tooth having a vertical wall and a rearwardly slanted top surface by a given amount and the ratchet tooth slides down the slanted top surface until it is adjacent a vertical wall of a next ratchet tooth in a ratchet tooth assembly to move the piston forward; and
   c. the dispensing apparatus includes an exterior surface with a rear opening and a front tip dispensing opening and surrounding an interior chamber which receives the ratchet mechanism which also has a resetting bar at its end which extends out the opening in the rear end of the dispensing apparatus so that the entire operating mechanism is be pulled backward in the interior chamber of the dispensing apparatus for the insertion of a fresh single use cartridge after a specific single use cartridge has been used up, the dispensing apparatus includes the interior chamber which contains the operating mechanism where the piston is adjacent an interior opening where the single use cartridge is inserted, the dispensing apparatus includes an interior cylindrical sidewall and an exterior cylindrical wall and an open front through which the front tip of the cartridge extends, and a back pushing member which is used to push the cartridge forward along with the operating mechanism to push the piston forward to enable the piston to move into the pocket against the back of the plunger and dispense the compound through the opening in the nozzle tip of the cartridge.

14. The apparatus in accordance with claim 13, further comprising: the operating mechanism further includes a pushed down tooth operator which is pushed down by the back pushing member and a tooth operating mechanism which pushes down on the moving ratchet tooth which sequentially engages each ratchet tooth, the moving ratchet tooth engaging member also has a spring mechanism which causes the moving ratchet tooth engaging member to move upwardly after it engages a ratchet tooth and moves it forward and is adjacent a vertical wall so it is moved upwardly to come in contact with the next slanted top wall of a ratchet tooth, and when a downward force from the back pushing member is exerted on and pushed down on the tooth operator which in turn exerts a downward force on the moving ratchet tooth engaging member, the member engages a downward sloped wall of a ratchet tooth and slides downwardly against the ratchet to move the ratchet forward by the given distance of the downward sloped wall until it arrives at the vertical wall of the next ratchet tooth and the spring mechanism causes the moving ratchet tooth engaging member to be pushed upwardly to come in contact with the next top sloped wall of the next ratchet tooth so that a downward force from the pushed down tooth operator causes the ratchet tooth to slide downwardly against the next sloped top or the next ratchet tooth and therefore move the ratchet forward, thereby moving the pistons forward.

15. The apparatus in accordance with claim 14, further comprising:
   a. the ratchet tooth assembly includes ratchet teeth is affixed to and is part of a longitudinal bar surrounded by a compression spring affixed to a plate which is attached to a rear ratchet tooth housing which includes rear ratchet teeth having a rear vertical wall and a rear slanted wall for each ratchet tooth with an inverted rear ratchet tooth engaging member with an upside down spring mechanism so that as the first ratchet mechanism is moved forwardly the bar moves forwardly causing a plate to which the bar is attached to move forwardly which in turn causes a compression housing plate to move forwardly which in turn causes the rear ratchet tooth engaging member to move forwardly and downwardly against and to engage a rear slanted top wall of a rear ratchet tooth until it comes in contact with a rear ratchet tooth vertical wall, the upside down spring causes the moving ratchet tooth engaging member to move upwardly after it engages a ratchet tooth and moves it forward and is adjacent a vertical wall so it is moved upwardly to come in contact with the next rear slanted top wall of a rear ratchet tooth; and
   b. a main compression spring and a rear ratchet tooth compression spring surrounding rear ratchet tooth assembly are compressed and after the cartridge is used up, the back resetting member is pulled away from the back wall, overcoming the compression force of compression springs to reset the entire ratchet tooth assemblies so the pistons are moved away from the front opening to leave the opening into which a new cartridge can be inserted.

16. The apparatus in accordance with claim 13, further comprising:
   a. the exterior wall of the single use cartridge includes an anti-rotation slit; and
   b. the opening in the dispensing apparatus into which the single use cartridge is inserted includes an anti-rotation shaft inserted into the anti-rotation slit.

17. The apparatus in accordance with claim 13, further comprising: the interconnecting section is frustum shaped with a widened end adjacent a body of the single use cartridge and a narrow end adjacent the nozzle tip of the single use cartridge.

18. The apparatus in accordance with claim 13, further comprising:
   a. a straight applicator which includes an exterior surface and an interior chamber which has a widened end with interior threads surrounding a rear opening by which the straight applicator is threaded onto the exterior threads of the nozzle tip of the single use cartridge and the compound is pushed out a front opening in the straight nozzle.

19. The apparatus in accordance with claim 13, further comprising:
   a. a horn-shaped applicator which has an exterior wall and an interior chamber which has a rear opening and a rear interior wall having threads adjacent the rear opening by which the horn shaped nozzle is threaded onto the exterior threads of the nozzle tip of the single use cartridge and the compound is pushed out of an opening in the horn shaped applicator.

20. The apparatus in accordance with claim 13, further comprising: the compounds are selected from the group consisting of tooth whitening compounds, dental bonding and filling compounds, adhesive compounds, jells, creams, and finely ground powders.

21. An apparatus for removably retaining a single use cartridge and dispensing compounds from the single use cartridge, comprising:
   a. a single use cartridge having an exterior surface which surrounds an interior circumferential wall surrounding at least one interior chamber and a rear opening leading to the at least one interior, at least one compound retained within the at least one chamber, a plunger having front interior surfaces aligned with the at least one interior chamber and having sidewalls which serve as a seal against the interior circumferential wall to prevent at least one compound from flowing out of the rear opening, the plunger having at least one pocket, the exterior surface leading to a nozzle having a cylindrical surface extending from the frustum shaped section to a dispensing nozzle tip having threads on an exterior surface of the dispensing nozzle tip and a frangible seal on a front end of the dispensing nozzle tip to retain the at least one compound in a sealed condition within the at least one interior chamber, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the cartridge;
   b. an operating mechanism for the at least one chamber single use cartridge, the operating mechanism including at least one piston which is used to engage the plunger and a ratchet mechanism which is used to move the at least one pistons in a forward direction to push the plunger forwardly to dispense the compounds from the single use cartridge when the single use cartridge is placed in the dispensing apparatus; and c. the dispensing apparatus includes an exterior surface with a rear opening and a front tip dispensing opening and surrounding an interior chamber which receives the ratchet mechanism which also has a resetting bar at its end which extends out the opening in the rear end of the dispensing apparatus so that the entire operating mechanism is be pulled backward in the interior chamber of the dispensing apparatus for the insertion of a fresh single use cartridge after a specific single use cartridge has been used up, the dispensing apparatus includes the interior chamber which contains the operating mechanism where the at least one piston is adjacent an interior opening where the single use cartridge is inserted, the dispensing apparatus includes an interior cylindrical sidewall and an exterior cylindrical wall and an open front through which the front tip of the cartridge extends, and a mechanism which is used to push the ratchet mechanism forward along with the mechanism to push the at least one piston forward to enable the at least one piston to move into the pocket against the back of the plunger and dispense the compound through the opening in the nozzle tip of the cartridge.

22. The apparatus in accordance with claim 21, further comprising: the compounds are selected from the group consisting of tooth whitening compounds, dental bonding and filling compounds, adhesive compounds, jells, creams, and finely ground powders.

* * * * *